(12) United States Patent
Postma et al.

(10) Patent No.: US 12,419,815 B2
(45) Date of Patent: Sep. 23, 2025

(54) MICROCAPSULE COMPOSITIONS STABILIZED WITH VISCOSITY CONTROL AGENTS

(71) Applicant: International Flavors & Fragrances Inc., New York, NY (US)

(72) Inventors: Djurre Sijbren Postma, Zeewolde (NL); Yabin Lei, Union Beach, NJ (US); Hui Min Lee, Singapore (SG); Daniel Kaiping Lee, Union Beach, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 569 days.

(21) Appl. No.: 17/314,314

(22) Filed: May 7, 2021

(65) Prior Publication Data

US 2021/0268467 A1  Sep. 2, 2021

Related U.S. Application Data

(63) Continuation of application No. 16/334,038, filed as application No. PCT/US2017/051916 on Sep. 15, 2017.

(60) Provisional application No. 62/395,586, filed on Sep. 16, 2016.

(51) Int. Cl.

| | |
|---|---|
| A61K 8/11 | (2006.01) |
| A01N 25/28 | (2006.01) |
| A23P 10/30 | (2016.01) |
| A61K 8/04 | (2006.01) |
| A61K 8/30 | (2006.01) |
| A61K 8/64 | (2006.01) |
| A61K 8/73 | (2006.01) |
| A61K 8/81 | (2006.01) |
| A61K 8/84 | (2006.01) |
| A61K 8/87 | (2006.01) |
| A61K 8/88 | (2006.01) |
| A61K 8/96 | (2006.01) |
| B01J 13/02 | (2006.01) |
| B01J 13/14 | (2006.01) |
| C08G 18/32 | (2006.01) |
| C08G 18/38 | (2006.01) |
| C08G 18/64 | (2006.01) |
| C08G 18/76 | (2006.01) |
| C08G 18/78 | (2006.01) |
| C08G 18/79 | (2006.01) |
| C08G 18/80 | (2006.01) |
| C08L 5/00 | (2006.01) |
| C08L 33/08 | (2006.01) |
| C08L 33/26 | (2006.01) |
| C08L 61/28 | (2006.01) |
| C11D 3/00 | (2006.01) |
| C11D 3/50 | (2006.01) |
| C11D 17/00 | (2006.01) |
| D06M 23/12 | (2006.01) |

(52) U.S. Cl.
CPC ................ *A61K 8/11* (2013.01); *A01N 25/28* (2013.01); *A61K 8/04* (2013.01); *A61K 8/044* (2013.01); *A61K 8/30* (2013.01); *A61K 8/64* (2013.01); *A61K 8/645* (2013.01); *A61K 8/73* (2013.01); *A61K 8/732* (2013.01); *A61K 8/8152* (2013.01); *A61K 8/8158* (2013.01); *A61K 8/84* (2013.01); *A61K 8/87* (2013.01); *A61K 8/88* (2013.01); *A61K 8/96* (2013.01); *B01J 13/02* (2013.01); *B01J 13/14* (2013.01); *C08G 18/3228* (2013.01); *C08G 18/3231* (2013.01); *C08G 18/325* (2013.01); *C08G 18/3271* (2013.01); *C08G 18/3821* (2013.01); *C08G 18/3848* (2013.01); *C08G 18/6423* (2013.01); *C08G 18/6446* (2013.01); *C08G 18/6484* (2013.01); *C08G 18/7664* (2013.01); *C08G 18/7831* (2013.01); *C08G 18/792* (2013.01); *C08G 18/794* (2013.01); *C08G 18/8029* (2013.01); *C08L 5/00* (2013.01); *C08L 33/08* (2013.01); *C08L 61/28* (2013.01); *C11D 3/0015* (2013.01); *C11D 3/505* (2013.01); *C11D 17/0013* (2013.01); *C11D 17/0039* (2013.01); *A23P 10/30* (2016.08); *C08L 33/26* (2013.01); *D06M 23/12* (2013.01)

(58) Field of Classification Search
None
See application file for complete search history.

(56) References Cited

U.S. PATENT DOCUMENTS

| | | | |
|---|---|---|---|
| 4,785,048 A | 11/1988 | Chao | |
| 9,738,817 B2 | 8/2017 | Zajaczkowski et al. | |
| 10,369,094 B2 * | 8/2019 | Lei ............................ | A61K 8/11 |
| 11,224,569 B2 * | 1/2022 | Lei ............................ | A61Q 5/12 |

(Continued)

FOREIGN PATENT DOCUMENTS

| | | |
|---|---|---|
| WO | 2014011860 A2 | 1/2014 |
| WO | 2016144798 A1 | 9/2016 |

OTHER PUBLICATIONS

Extended European Search Report dated Apr. 20, 2020 for EP 17851666.2, filed Sep. 15, 2017.

(Continued)

*Primary Examiner* — Sin J Lee

(57) ABSTRACT

Disclosed are microcapsule compositions each comprising a microcapsule suspended in an aqueous phase and a viscosity control agent, wherein the viscosity control agent is an acrylate copolymer, a cationic acrylamide copolymer, or a polysaccharide. Also disclosed are consumer products containing such a microcapsule composition.

5 Claims, No Drawings

(56) References Cited

U.S. PATENT DOCUMENTS

| | | | |
|---|---|---|---|
| 2007/0042182 A1 | 2/2007 | Markus et al. | |
| 2009/0311336 A1 | 12/2009 | Jones et al. | |
| 2013/0109569 A1 | 5/2013 | Dave et al. | |
| 2013/0337023 A1 | 12/2013 | Lei et al. | |
| 2014/0044760 A1 | 2/2014 | Lei et al. | |
| 2015/0252312 A1 | 9/2015 | De Villeneuve et al. | |
| 2016/0158121 A1 | 6/2016 | Lei et al. | |
| 2016/0184196 A1 | 6/2016 | Baxter et al. | |
| 2016/0256365 A1 | 9/2016 | Dihora et al. | |
| 2017/0042778 A1 | 2/2017 | Carle et al. | |
| 2017/0283744 A1 | 10/2017 | Antir et al. | |
| 2018/0064615 A1* | 3/2018 | Brahms | C11D 11/0017 |
| 2018/0085291 A1 | 3/2018 | Sasaki et al. | |
| 2019/0159979 A1* | 5/2019 | Brahms | A61K 9/4816 |
| 2019/0184364 A1* | 6/2019 | Brahms | B01J 13/025 |
| 2019/0231658 A1* | 8/2019 | Lei | A61K 8/817 |
| 2022/0008886 A1* | 1/2022 | Lei | A61K 8/11 |

OTHER PUBLICATIONS

International Preliminary Report on Patentability in PCT/US2017/051916 dated Mar. 19, 2019.
International Search Report and Written Opinion in PCT/US2017/051916 dated Jan. 9, 2018.
Office Communication dated Aug. 9, 2019 from U.S. Appl. No. 16/334,038, filed Mar. 18, 2019.
Office Communication dated Mar. 12, 2020 from U.S. Appl. No. 16/334,038, filed Mar. 18, 2019.
Office Communication dated Jan. 21, 2021 from U.S. Appl. No. 16/334,038, filed Mar. 18, 2019.

* cited by examiner

MICROCAPSULE COMPOSITIONS STABILIZED WITH VISCOSITY CONTROL AGENTS

INTRODUCTION

This application is a continuation application of U.S. patent application Ser. No. 16/334,038, filed Mar. 18, 2019, which is the National Stage of International Application No. PCT/US2017/051916, filed Sep. 15, 2017, which claims the benefit of priority from U.S. Provisional Application Ser. No. 62/395,586, filed Sep. 16, 2016, the contents of which are incorporated herein by reference in their entireties.

BACKGROUND

Microcapsules are useful in a variety of applications where there is a need to deliver, apply, or release a fragrance or other active material in a time-delayed and controlled manner.

Conventional microcapsule compositions contain microcapsules dispersed in an aqueous phase. They tend to form gel, separate into layers, release the active material prematurely, etc. See US 2014/0287008 and WO 2015/023961. Certain microcapsule compositions have been developed to improve the stability via engineering a more robust microcapsule wall. See US 2014/0044760, WO 2014/011860, and US 2013/0337023. However, these microcapsule compositions still face stability issues including short storage lifetime, gel formation during transportation in a harsh temperature, and instability in consumer products.

There is a need to develop a stable microcapsule composition that can be stored for an extended period of time and provide a long shelf life in consumer products.

SUMMARY OF THE INVENTION

This invention is based on the discovery that certain viscosity control agents can stabilize microcapsule compositions.

Accordingly, one aspect of this invention relates to a microcapsule composition comprising (i) a microcapsule suspended in an aqueous phase and (ii) a viscosity control agent, in which the viscosity control agent is an acrylate copolymer, a cationic acrylamide copolymer, or a polysaccharide.

Examples of the acrylate copolymer are copolymers of acrylic acid and acrylate, acrylate/$C_{10}$-$C_{30}$ alkyl acrylate cross-polymers, and combination thereof.

Useful microcapsules include those having a microcapsule wall and a microcapsule core encapsulated by the microcapsule wall. The microcapsule wall is typically formed of an encapsulating polymer selected from the group consisting of a polyacrylate, polyurea, polyurethane, polyacrylamide, polyester, polyether, polyamide, poly(acrylate-co-acrylamide), starch, silica, gelatin and gum Arabic, alginate, chitosan, polylactide, a melamine-formaldehyde polymer, poly(urea-formaldehyde), and combinations thereof. The microcapsule core can contain an active material selected from the group consisting of a fragrance, pro-fragrance, flavor, malodor counteractive agent, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, nanometer to micron size inorganic solid, polymeric or elastomeric particle, taste modulator, cell, probiotic, and combinations thereof.

The microcapsule compositions described above can further contain a dispersant such as a polyvinyl alcohol, polystyrene sulfonate, carboxymethyl cellulose, sodium polystyrene sulfonate, alkylnaphthalenesulfonate formaldehyde condensate, polyvinylpyrrolidone, copolymer of vinyl pyrrolidone and quaternized dimethylaminoethyl methacrylate, and combinations thereof.

When the encapsulating polymer is a polyurea or polyurethane, the polyurea is usually a reaction product of a polyfunctional isocyanate and a polyfunctional amine in the presence of an alkylnaphthalenesulfonate formaldehyde condensate and polyvinylpyrrolidone, and the polyurethane is a reaction product of a polyfunctional isocyanate and a polyfunctional alcohol as a cross-linking agent in the presence of an alkylnaphthalenesulfonate formaldehyde condensate and polyvinylpyrrolidone.

Suitable polyfunctional isocyanates include, but are not limited to, an aromatic polyfunctional isocyanate, aliphatic polyfunctional isocyanate, or combination thereof. Examples of the aromatic polyfunctional isocyanate contain a phenyl, tolyl, xylyl, naphthyl, or diphenyl moiety, or a combination thereof, such as polymeric methylene diphenyl diisocyanate, polyisocyanurates of toluene diisocyanate, trimethylol propane-adducts of toluene diisocyanate, trimethylol propane-adducts of xylylene diisocyanate, and combinations. Nonlimiting examples of the aliphatic polyfunctional isocyanate include trimers (symmetric or asymmetric) of hexamethylene diisocyanate, trimers of isophorone diisocyanate, biurets of hexamethylene diisocyanate, and combinations thereof.

Exemplary polyfunctional amines are hexamethylenediamine, hexaethylenediamine, ethylenediamine, 1,3-diaminopropane, 1,4-diamino-butane, diethylenetriamine, pentaethylenehexamine, 1,6-diaminohexane, hydrazine, 1,4-diaminocyclohexane and 1,3-diamino-1-methylpropane, bis(3-aminopropyl)amine, bis(hexamethylene)triamine, tris (2-aminoethyl)amine, triethylene-tetramine, N,N'-bis(3-aminopropyl)-1,3-propanediamine, tetraethylenepentamine, branched polyethylenimine, chitosan, nisin, gelatin, 1,3-diamino-guanidine, 1,1-dimethylbiguanide, guanidine, arginine, lysine, ornithine, histidine, amino-2-methyl-1-propanol, or a combination thereof.

When the alkylnaphthalenesulfonate formaldehyde condensate and polyvinylpyrrolidone are used as the dispersant, each of them can be, independently, present at a level of 0.1 to 5% by weight of the microcapsule composition. The ratio between the alkylnaphthalenesulfonate formaldehyde condensate and polyvinylpyrrolidone can range from 10:1 to 1:10.

The encapsulating polymer can be a polyurea that is a reaction product of a polyisocyanate and a polyamine, in which the polyisocyanate contains a trimethylol propane-adduct of toluene diisocyanate or a trimethylol propane-adduct of xylylene diisocyanate, and the polyamine is diethylenetriamine, bis(3-aminopropyl)amine, bis(hexamethylene)triamine, tris-(2-aminoethyl)amine, triethylenetetramine, N,N'-bis(3-aminopropyl)-1,3-propanediamine, tetraethylene-pentamine, pentaethylenehexamine, branched polyethylenimine, chitosan, nisin, gelatin, 1,3-diaminoguanidine monohydrochloride, 1,1-dimethylbiguanide hydrochloride, guanidine carbonate, or a mixture thereof.

The microcapsule compositions can further comprise a polyvinyl alcohol, polystyrene sulfonate, carboxymethyl cellulose, alkylnaphthalenesulfonate formaldehyde condensate, copolymer of vinyl pyrrolidone and quaternized dimethylaminoethyl methacrylate, or combination thereof.

Optionally, the microcapsule compositions contains a stabilizing agent selected from the group consisting of hexamethylene diamine, hexaethylenediamine, ethylenediamine, 1,3-diaminopropane, 1,4-diamino-butane, diethylenetriamine, pentaethylenehexamine, bis(3-aminopropyl) amine, bis(hexamethylene)triamine, tris(2-aminoethyl) amine, triethylene-tetramine, N,N'-bis(3-aminopropyl)-1,3-propanediamine, tetraethylenepentamine, branched polyethylenimine, chitosan, nisin, gelatin, 1,3-diamino-guanidine, 1,1-dimethylbiguanide, guanidine, arginine, lysine, ornithine, histidine, amino-2-methyl-1-propanol, 5-chloro-2-methyl-4-isothiazolin-3-one, 2-methyl-4-isothiazolin-3-one, iodopropynyl butylcarbamate, phenoxyethanol, and combinations thereof.

A deposition aid is also an optional component in the microcapsule compositions. Examples include polyquaternium-4, polyquaternium-5, polyquaternium-6, polyquaternium-7, polyquaternium-10, polyquaternium-16, polyquaternium-22, polyquaternium-24, polyquaternium-28, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, and combinations thereof.

In some embodiments, the microcapsule composition further contains one or more free fragrances (e.g., a first, second, third, and/or fourth fragrances) and/or one or more additional microcapsules (e.g., a second, third, and/or fourth microcapsules).

In some microcapsule compositions, the encapsulating polymer is a melamine-formaldehyde polymer including a melamine-formaldehyde polymer crosslinked with an acrylate copolymer such as poly(acrylic acid-acrylamide) and poly(acrylic acid-acrylate).

In some microcapsule compositions, the viscosity control agent is a copolymer of acrylic acid and acrylate present at a level of 0.1 to 5% (e.g., 0.2 to 2%) by weight of the microcapsule composition. In other microcapsule compositions, the viscosity control agent is xanthan gum, which is a polysaccharide.

Any microcapsule compositions described above can be in a slurry or a solid form. The latter is typically prepared by drying such as spray drying.

Also within the scope of this invention is a consumer product containing the above-described microcapsule composition. Exemplary consumer products are a shampoo, a hair conditioner, a hair rinse, a hair refresher, a hair fixative or styling aid, a hair bleach, a hair dye or colorant, a soap, a body wash, a cosmetic preparation, an all-purpose cleaner, a bathroom cleaner, a floor cleaner, a window cleaner, a bath tissue, a paper towel, a disposable wipe, a diaper rash cream or balm, a baby powder, a diaper, a bib, a baby wipe, an oral care product, a tooth paste, an oral rinse, an tooth whitener, a denture adhesive, a chewing gum, a breath freshener, an orally dissolvable strips, a chewable candy, a hard candy, a hand sanitizer, an anti-inflammatory balm, an anti-inflammatory ointment, an anti-inflammatory spray, a health care device, a dental floss, a toothbrush, a tampon, a feminine napkin, a personal care product, a sunscreen lotion, a sunscreen spray, a wax-based deodorant, a glycol type deodorant, a soap type deodorant, a facial lotion, a body lotion, a hand lotion, a body powder, a shave cream, a bath soak, an exfoliating scrub, a foot cream, a facial tissue, a cleansing wipe, a fabric care product, a fabric softener, a fabric refresher, an ironing water, a liquid laundry detergent, a liquid dish detergent, an automatic dish detergent, a unit dose tablet or capsule, a scent booster, a drier sheet, a fine fragrance, a solid perfume, a powder foundation, a liquid foundation, an eye shadow, a lipstick or lip balm, an Eau De Toilette product, a deodorant, a rug deodorizer, a candle, a room deodorizer, a disinfectant, an aerosol antiperspirant, a stick antiperspirant, a roll-on antiperspirant, an emulsion spray antiperspirant, a clear emulsion stick antiperspirant, a soft solid antiperspirant, an emulsion roll-on antiperspirant, a clear emulsion stick antiperspirant, an opaque emulsion stick antiperspirant, a clear gel antiperspirant, a clear stick deodorant, a spray deodorant, a baked product, a bread, a dry biscuit, a cake, a cookie, a chip, a popcorn, a pretzel, an extruded snack, a breakfast cereal, a muesli bar, a precooked finished rice product, an alcoholic or non-alcoholic beverage, a spice blend, a soup, a sauce, a stew, a frozen entrée, a yogurt, an ice cream, a bean curd, a cheese, a soya protein product, a meat product, an egg product, a mayonnaise, a remoulade, a dressing, a seasoning preparation, a fruit preparation, or a vegetable preparation.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The terms "capsule" and "microcapsule" herein are used interchangeably.

The terms "g," "mg," and "µg" refer to "gram," "milligram," and "microgram," respectively. The terms "L" and "mL" refer to "liter" and "milliliter," respectively.

The details of one or more embodiments of the invention are set forth in the description below. Other features, objects, and advantages of the invention will be apparent from the description and the claims.

DETAILED DESCRIPTION OF THE INVENTION

The microcapsule compositions are stabilized by a viscosity control agent for at least 4 weeks (e.g., at least 6 weeks, at least 8 weeks, 4 weeks to two years, 4 week to one year, and 4 to 26 weeks) when being stored at 25 or 45° C.

The stability is measure by both the viscosity and water separation. Known microcapsule compositions tend to form into gels, making them unsuitable for use in consumer products. When turning into a gel, the viscosity of the composition increases to 3000 centipoise (cP) or greater 6000 cP. The microcapsule is considered stable if it does not gel out and has a viscosity of 3000 cP or less (e.g., 2500 cP or less and 2000 cP or less).

Another measurement of stability is the degree of the separation of water from the microcapsule. Initially, the microcapsule composition is emulsion-like dispersion (i.e., a colloidal suspension) in which the microcapsules are evenly dispersed in the water phase. Over storage, the microcapsules can flocculate and water can separate out from the composition. Such separation will require additional process to turn the composition to a homogenous suspension, during which undesirable microcapsule bursting and fragrance leakage are observed. The microcapsule composition is deemed stable if 20% or less (e.g., 10% or less and 5% or less) water by volume of the composition is separated.

Typically, the microcapsule composition of this invention is a microcapsule slurry containing one or more microcapsules dispersed in an aqueous phase.

The one or more microcapsules each have a microcapsule core and a microcapsule wall encapsulating the microcapsule core. In some embodiments, the microcapsule wall is free of a viscosity control agent, e.g., an acrylate copolymer (such as a copolymer of acrylic acid and acrylate, and acrylate/$C_{10}$-$C_{30}$ alkyl acrylate cross-polymer), a cationic acrylamide copolymer, or a polysaccharide (such as xanthan gum).

In some embodiments, the microcapsule is present at a level of 10 to 70% (e.g., 20 to 70% and 30 to 60%) by weight of the stable microcapsule compositions described above.

The viscosity control agent is not part of the microcapsule wall. It is dispersed homogenously in the aqueous phase and stays outside of the microcapsule wall. In some embodiments, the viscosity control agent is present at a level of 0.01 to 10% (e.g., 0.1 to 5%, 0.2 to 5%, 0.2 to 2%, 0.5 to 1.5%, 0.01 to 0.1%, and 0.02 to 0.05%).

The microcapsule compositions of this invention typically have a pH value of 2-10 (e.g., 3-9, 4-8, 5-8, and 6-7.5). The pH value can be adjusted by adding an acid or base.

The microcapsule compositions of this invention find their utility in a wide range of consumer applications, e.g., personal care products including shampoos, hair conditioners, hair rinses, hair refreshers; personal wash such as bar soaps, body wash, personal cleaners and sanitizers, hydro-alcoholic formulations; fabric care such as fabric refreshers, softeners and dryer sheets, ironing water, industrial cleaners, liquid and powder detergent including unit dose capsules, rinse conditioners, and scent booster products; fine fragrances; an Eau De Toilette products; deodorants; roll-on products, and aerosol products.

The components of the microcapsule composition are described in detail below.

Viscosity Control Agent. Any viscosity control agent can be used in this invention. It is added to the microcapsule composition to achieve a desired viscosity of the composition so that the microcapsule is dispersed in the composition for a pro-longed period of time.

The viscosity control agent typically disperses homogeneously in the microcapsule slurry and outside of the microcapsule wall of the microcapsules in the composition of this invention.

Suitable viscosity control agents include an acrylate copolymer, a cationic acrylamide copolymer, a polysaccharide, or a combination thereof.

Acrylate Copolymers. Commercially available acrylate copolymers include those under the trade name ACULYN™ (from Dow Chemical Company) such as ACULYN™ 22 (a copolymer of acrylates and steareth-20 methacrylate), ACULYN™ 28 (a copolymer of acrylate and beheneth-25 methacrylate), ACULYN™ 33 (a copolymer of acrylic acid and acrylate), ACULYN™ 38 (a crosspolymer of acrylate and vinyl neodecanoate), and ACULYN™ 88 (a crosspolymer of acrylate and steareth-20 methacrylate). Particularly useful acrylate copolymers are anionic acrylate copolymer such as ACULYN™ 33, an alkali-soluble anionic acrylic polymer emulsion (ASE), which is synthesized from acrylic acid and acrylate comonomers through emulsion polymerization. The commercial product of ACULYN™ 33 contains 28% of the polymer in water, has a pH of 3, a density of 1.05 g/mL, an equivalent weight of 218 (the equivalent weight refers to grams of dry polymer neutralized by 1 equivalent, i.e., 40 grams of sodium hydroxide), and a viscosity of 10 cP. In one embodiment, the acrylate copolymer has the following structure:

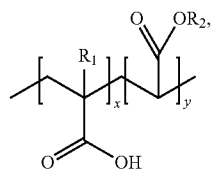

in which, $R_1$ is H or a $C_1$-$C_{24}$ (e.g., $C_1$-$C_{10}$ and $C_1$-$C_6$) alkyl, $R_2$ is a $C_1$-$C_{24}$ (e.g., $C_1$-$C_{10}$ and $C_1$-$C_6$) alkyl, x is an integer selected from 1-4100, and y is an integer selected from 1-4100. The molecular weight of the acrylate copolymer is 200-10000000 (e.g., 500-5000000, 1000-1000000, and 2000 to 500000).

CARBOPOL® polymers are also suitable acrylate copolymer useful in this invention. Examples are CARBOPOL® ETD 2020 polymer (a crosspolymer of acrylate and $C_{10}$-$C_{30}$ alkyl acrylate), CARBOPOL® ETD 2691, CARBOPOL® ETD 2623 (a crosslinked acrylate copolymer), Carbomers. Carbomer (polyacrylic acid) can also be used as viscosity control agents. Carbomer codes (672, 690, 910, 934, 934P, 940, 941, 1342, 1662) are an indication of molecular weight and the specific components of the polymer. Their molecular weight ranges from 100000 to 3,000,000 (Carbomer 672, M.W. 3,000,000; Carbomer 910, M.W., 750,000; Carbomer 934, M.W., 500000; Carbomer 940, M.W. 4000000; Carbomer 941, M.W. 1250000; and Carbomer 1662, M.W., 4,000,000). Carbomer polymers are commercially available, e.g., under the trade name CARBOPOL® from Lubrizol Corporation.

Polysaccharides. Polysaccharides are another class of agents suitable for viscosity control agents. Commonly used polysaccharides include starches, pectin, and vegetable gums such as alginin, guar gum, locust bean gum, and xanthan gum (e.g., KELTROL® T, 80-mesh food-grade, commercially available from CP Kelco, Atlanta, Ga.).

Cationic Acrylamide. Cationic acrylamide copolymers can also be used as viscosity control agents. These cationic cross-linked polymers are derivable from the polymerization of from 5 to 100 mole percent of cationic vinyl addition monomer, from 0 to 95 mole percent of acrylamide and from 50 to 1000 ppm of a difunctional vinyl addition monomer cross-linking agent. Preferred polymers are cross-linked copolymers of acrylamide and methacrylate cross-linked with a difunctional vinyl addition monomer, such as methylene bisacrylamide. Particularly preferred polymers are copolymers of 20% acrylamide and 80% MADAM methyl chloride (MADAM: dimethyl amino ethyl methacrylate) cross-linked with from 450 to 600 ppm of methylene bisacrylamide. In one embodiment, the cationic acrylamide copolymer is a cationic copolymer obtained by Hofmann rearrangement in aqueous solution in the presence of an alkali and/or alkaline earth hydroxide and an alkali and/or alkaline earth hypohalide, on a base copolymer comprising: (i) at least 5 mole % of a non-ionic monomer selected from the group consisting of acrylamide, methacrylamide, N,N- dimethylacrylamide, acrylonitrile, and combinations thereof; and (ii) at least one comonomer selected from the group consisting of unsaturated cationic ethylenic comonomer, non-ionic comonomer, or combinations thereof, provided that the non-ionic comonomer is not acrylamide, methacrylamide, N,N-dimethylacrylamide, or acrylonitrile. The cationic copolymer thus obtained has a desalination coefficient (Cd) of greater than 0.6 (e.g., greater than 0.65 and greater than 0.7). Cd is calculated as Real polymeric active matter (% by weight of the copolymer)×Polymer filler density Conductivity of the solution containing 9% of active matter. See also U.S. Pat. No. 8,242,215. The unsaturated cationic ethylenic comonomer can be selected from the group consisting of dialkylaminoalkyl(meth)acrylamide monomers, diallylamine monomers, methyldiallylamine monomers, and quaternary ammonium salts or acids thereof, such as dimethyldiallylammonium chloride (DADMAC), acrylamidopropyltrimethyl-ammonium chloride (APTAC), methacrylamidopropyltrimethylammonium chloride (MAPTAC). Examples of the non-ionic comonomer are N-vinyl acetamide, N-vinyl formamide, N-vinylpyrrolidone, vinyl acetate, and combinations thereof. The base copolymer is preferably branched in the presence of a branching agent selected from the group consisting of methylene bisacrylamide, ethylene glycol di-acrylate, polyethylene glycol dimethacrylate, diacrylamide, cyanomethylacrylate, vinyloxyethylacrylate, vinyloxyethylmethacrylate, triallylamine, formaldehyde, glyoxal, and a glycidylether type compound. More examples of the cationic acrylamide copolymers can be found in U.S. Pat. No. 8,242,215. Such materials are commercially available from SNF Floerger under the trade names Flosoft™ S 200, Flosoft™ FS 222, and Flosoft™ FS 228. See also WO 2007141310, US 20060252668, and US 20100326614.

Additional examples of the viscosity control agent include polypropylene glycol, materials containing propylene oxide groups, materials containing polyethylene oxide groups, polysorbate 20 (TWEEN® 20), Poloxamer 124 (PLURONIC® L44) polyethylene oxide-polypropylene oxide block copolymer having the formula $(EO)x(PO)y(EO)z$ with $x=11\pm3$, $z=11\pm3$ and $y=21\pm5$, Poloxamer L35, Poloxamer L31, polyethylene glycol 55 (PEG-55), glycerin, diethylene glycol, CREMOPHOR® polyoxyethyleneglyceroltriricinoleat, GLUCAM® P-10 propylene glycol ether of methyl glucose with 10 polypropylene oxide units, PLURIOL® E300 alkoxylates based on ethylene oxide and propylene oxide, sodium cumene sulfonate (SCS), sodium xylene sulfonate (SXS), GLUCAM® P-20 propylene glycol ether of methyl glucose with 20 polypropylene oxide units, GLUCAM® E-20 ethylene glycol ether of methyl glucose with 20 polyethylene oxide units, GLUCAM® E-10 ethylene glycol ether of methyl glucose with 10 polyethylene oxide units, and short chain ethoxylated propoxylated alcohols such as PPG2-Buteth-3, PPG3-Buteth-5, or PPG5-Buteth-7. More viscosity control agents are described in U.S. Pat. No. 6,465,416 and US 20060252668.

The molecular weight of the polymeric viscosity control agent varies from 1000 to 10000000 (e.g., 2000 to 6000000, 3000 to 5000000, 10000 to 5000000, and 50000 to 5000000).

The amount of the viscosity control agent can be any desired amount to obtain the desired viscosity of the composition. In certain embodiments, the amount is 0.01 to 20% by weight of the composition. In other embodiments, the amount is 0.1 to 10%, 0.2 to 8%, 0.2 to 5%, 0.28 to 1.4%, and 0.021 to 0.045%.

A person skilled in the art can determine the amount of the viscosity control agent needed so that the microcapsule composition has a viscosity that allows the composition to be pourable, which is usually below 10 Pa's (e.g., less than 5 Pa-s, less than 1.5 Pa-s, less than 1 Pa-s, less than 0.750 Pa's, less than 0.500 Pa-s, less than 0.100 Pa-s, less than 0.080, and less than 0.075 Pa's). Viscosity is measured following standard procedures in the art, e.g., using a Brookfield RVT Viscometer equipped with spindle 2 at 20 RPM at 25° C.

Clays. In addition, negatively charged clays can also be used as viscosity control agents. These clays contain fine particles having a net negative electrostatic charge on at least one surface of their sheets. The surface charge is usually balanced by the presence of charge balancing ions (sometimes called exchangeable ions, e.g., sodium and calcium) which are usually present between the layers of the clay and at the edges of the layers.

Preferred negatively charged clays are 2:1 phyllosilicates, in which the clay layers comprise two tetrahedral sheets sandwiching one octahedral sheet. Examples are smectite clays having the general formula $Al_2(Si_2O_5)_2(OH)_2 \cdot nH_2O$ or $Mg_3(Si_2O_5)_2(OH)_2 \cdot nH_2O$, and derivatives thereof, for example in which a proportion of the aluminum ions are replaced with magnesium ions or a proportion of the magnesium ions are replaced with lithium ions and/or some of the hydroxyl ions are replaced by fluoride ions; the derivatives may comprise a further metal ion to balance the overall charge.

The term smectite clays herein include both the clays in which aluminum oxide is present in a silicate lattice and the clays in which magnesium oxide is present in a silicate lattice. Typical smectite clay compounds include the dioctahedral minerals montmorillonite, beidellite, volchonskoites, and nontronite, and the trioctahedral minerals hectorite, saponite, and sauconite, particularly those having an alkali or alkaline earth metal ion within the crystal lattice structure. Preferred smectite clays are montmorillonite clays.

The montmorillonite clays typically have the general formula $HAlSi_2O_6$ but with variable Al—Si ratios, variable amounts of water and usually containing variable amounts of exchangeable cations. These clays can have alkali and alkaline earth metal cations as exchangeable ions. Examples include sodium and calcium montmorillonites. Another exemplary montmorillonite clay is an aluminous member of the group accorded the empirical Formula $(OH)_4Si_8(Al_{3.34}Mg_{0.66}Na_{0.66})O_{20}$. Both bentonite and hectorite are also members of the montmorillonite clays.

Commercially available montmorillonite clays include GELWHITE® series (highly purified montmorillonite clays) marketed as GELWHITE®-GP, GELWHITE®-H, and GELWHITE®-L by BYK Additives & Instruments, Germany. Other commercial products include Mineral Colloid BP, Mineral Colloid MO, GELWHITE® MAS 100 (sc), GELWHITE® MAS 101, GELWHITE® MAS 102, GELWHITE® MAS 103, BENTOLITE® WH, BENTOLITE® L10, BENTOLITE® H, BENTOLITE® L, PERMONT® SX10A, PERMONT® SC20, and PERMONT® HN24 (Southern Clay Products, Texas, USA); BENTONE® EW and BENTONE® MA (Dow Corning); Bentonite USP BL 670 and BENTOLITE® H4430 (Whitaker, Clarke & Daniels); Clarit 100 G1 and Clarit 1100 G1 (calcium bentonites from Sud Chemie AG); and VOLCLAY® 2 (sodium bentonite from Sud Chemie AG).

Examples of synthetic hectorites useful in the present invention include those products sold under the trade names LAPONITE® RD, LAPONITE® RDS, LAPONITE® XLG, LAPONITE® XLS, LAPONITE® D, LAPONITE® DF, LAPONITE® DS, LAPONITE® S and LAPONITE® JS (all from Southern Clay products, Texas, USA, a subsidiary of Rockwood).

Additional suitable smectite clays are disclosed in U.S. Pat. Nos. 3,862,058, 3,948,790, 3,954,632 and 4,062,647, and in EP0299,575A1, EP0313,146A1, and EP0352878B1.

Clays may be used as obtained from the supplier and may contain conventional additives such as, for example, disintegrating agents (also known as peptisers) and water of hydration. The clays may be used in their natural state or in a purified or semi-purified form, for example with the removal of mineral impurities.

The cation exchange capacity (CEC) of a clay is a well-known parameter and may be determined by well-established analytical techniques, including by electrodialysis, by exchange with ammonium ion followed by titration or by a methylene blue procedure, all as fully described in Grimshaw, "The Chemistry and Physics of Clays", pp. 264-265, Interscience (1971). It is customary to measure the cation exchange capacity of a clay in terms of milliequivalents per 100 g of dry clay (meq/100 g).

Preferred clays for use in the present invention have a cation exchange capacity of from 0.7 meq/100 g to 150 meq/100 g (e.g., 30 meq/100 g to 100 meq/100 g).

The clays preferably have a volume-based median particle diameter (D0.5) from 0.001 μm to 80 μm (e.g., 0.01 μm to 50 μm, 0.02 μm to 20 μm, and 0.05 to 5 μm). Particle diameters can be determined using a Malvern Mastersizer (Malvern Instruments, UK).

The permanent charges of the silicate layers in the clay particles result from isomorphous substitutions. However, the degree of substitution changes from layer to layer within certain limits so that the interlayer cation density also varies from interlayer space to interlayer space and may also vary in directions parallel to the layers (heterogeneous charge distribution). The distribution of the interlayer cation density can easily be determined by the alkylammonium method as described in Mermut & Lagaly (2001) Clays and Clay Minerals 49:393-397. The average layer charge of montmorillonite clays varies between 0.2 and 0.4 eq/formula unit (Si, Al)4010. Some montmorillonite clays have an average layer charges around 0.3 eq/formula unit. The surface charge can be in the range of 0.01 to 2 Coulomb/m$^2$ ("Cm$^{-2}$") (e.g., 0.02 to 1 Cm$^{-2}$ and 0.05 to 0.5 Cm$^{-2}$).

The level of the clay in the total composition is preferably from 0.01 to 10 wt % of the total composition (e.g., 0.05 to 2 wt %, 0.05 to 1%, 0.1 to 0.5%, and 0.1 to 0.3%).

In the compositions of the invention, the clay is advantageously present in the form of a dispersion (for example a sol or gel) or as a suspension.

Cationic Polyquaternium Polymers. Cationic polyquaternium (hereinafter "PQ") polymers can also be added to any of the microcapsule compositions described above. The PQ polymers are not viscosity control agents. They are used in combination with clays or other polymers described above. These polymers are often added to the composition of this invention as a deposition aid to assist the fragrance-containing microcapsules to deposit on treated surfaces such as textiles, hairs, furniture, floors, and skins.

Suitable cationic polymers are cationic polyquaternium polymers such as those listed in Table 1 below.

TABLE 1

| PQ | Description | Trade Name |
|---|---|---|
| 1 | Ethanol, 2',2',2"-nitrilotris-, polymer with 1,4-dichloro-2-butene and N,N,N',N'-tetramethyl-2-butene-1,4-diamine | POLYQUAD ® (Alcon) |
| 2 | Poly[bis(2-chloroethyl) ether-alt-1,3-bis[3-(dimethylamino)propyl]urea] | MIRAPOL ® A-15 |
| 4 | Hydroxyethyl cellulose dimethyl diallylammonium chloride copolymer; Diallyldimethylammonium chloride-hydroxyethyl cellulose copolymer | CELQUAT ® L-200, H-100, L-200 |
| 5 | Copolymer of acrylamide and quaternized dimethylammoniummethyl methacrylate | MERQUAT ® 5, Reten (Hercules) |
| 6 | Poly (diallyldimethylammonium chloride) | MERQUAT ® 100, 106, MIRAPOL ® 100 |
| 7 | Copolymer of acrylamide and diallyldimethylammonium chloride | MERQUAT ® 550, 550L, 550PR, S, 7SPR, 740, 2200, MIRAPOL ® 550, POLYQUART ® 770INA, CONDITIONEZE ® 7 |
| 8 | Methyl and Stearyl Dimethylaminoethyl Methacrylate Quaternized with Dimethyl Sulfate | |
| 9 | Polydimethylaminoethyl Methacrylate Quaternized with Methyl Bromide | |
| 10 | Quaternized hydroxyethyl cellulose | MERQUAT ® 10, CELQUAT ® SC-230M, SC-240C, SC-140C, UCARE ® Polymer |
| 11 | Copolymer of vinylpyrrolidone and quaternized dimethylaminoethyl methacrylate | Luviquat PQ 11PN, GAFQUAT ® 775N, 440, 734, 775 |
| 14 | Ethanaminium, N,N,N-Trimethyl-2-[(2-Methyl-1-Oxo-2-Propenyl)Oxy]-, Methyl Sulfate, Homopolymer | |

TABLE 1-continued

| PQ | Description | Trade Name |
|---|---|---|
| 15 | Ethanaminium, N,N,N-Trimethyl-2-[(2-Methyl-1-Oxo-2-Propenyl)Oxy]-, Chloride, Polymer with 2-Propenamide | ROHAGIT ® KF 720F (Rohm GmbH) |
| 16 | Copolymer of vinylpyrrolidone and Quaternized vinyl imidazole | Luviquat FC 370, HM 552, Style, FC 550, Excellence |
| 17 | Poly(Oxy-1,2-Ethanediyl(Dimethyliminio)-1,3-Propanediylimino(1,6-Dioxo-1,6-Hexanediyl)Imino-1,3-Propanediyl(Dimethyliminio)-1,2-Ethanediyl Dichloride | MIRAPOL ® AD |
| 18 | Poly[Oxy-1,2-ethanediyl( dimethyliminio)-1,3-propanediylimino-(1,6-dioxo-1,6-heptanediyl)imino-1,3-propanediyl(dimethyliminio)-1,2-ethanediyl dichloride] | Luviquat 500 |
| 19 | Ethenol, polymer with aminomethyloxirane | Arlatone PQ-220 (ICI Americas) |
| 20 | Ethenyl octadecyl ether, polymer with aminomethyloxirane | Arlatone PQ-225 |
| 24 | Cellulose,2-[2-Hydroxy-3-(Trimethylammonio)Propoxy]Ethyl Ether, Chloride (Similar to PQ-10) | Quatrisoft Polymer LM-200 (Dow Chemical) |
| 27 | Hexanediamide, N,N'-bis(3-(Dimethylamino)Propyl)-, Polymer with N,N'-bis(3-Dimethylamino)Propyl Urea and 1,1'-Oxybis(2-Chloroethane), Block | |
| 28 | Copolymer of vinylpyrrolidone and methacrylamidopropyl trimethylammonium | GAFQUAT ® HS-100, CONDITIONEZE ® NT-10 |
| 29 | Chitosan, 2,3-Dihydroxypropyl-2-Hydroxy-3-(Trimethylammonio)Propyl Ether, Chloride | Quaternized Chitosan |
| 30 | Ethanaminium, N-Carboxymethyl-N,N-Dimethyl-2-((2-Methyl-1-Oxo-2-Propenyl)Oxy)-, Inner Salt, Polymer with Methyl 2-Methyl-2-Propenoate | Mexomere PX (Chimex) |
| 31 | 2-Propenenitrile, Homopolymer, Hydrolyzed, Block, Reaction Products with N,N-Dimethyl-1,3-Propanediamine, Di-Et Sulfate-Quaternized | Hypan QT100 (Lipo) |
| 32 | Poly(acrylamide 2-methacryloxyethyltrimethyl ammonium chloride) (Similar to PQ-15) | COSMEDIA ® CTC (Cognis GmbH) - PQ-32 + other, SALCARE ® SC92 (Ciba Corp.) PQ-32 + other |
| 33 | Ethanaminium, N,N,N-Trimethyl-2-[1-Oxo-2-Propenyl)Oxy]-, Chloride, Polymer with 2-Propenamide | Lanoquat DES-50, ULTIMER ® CG-200 (Nalco), Sepigel Quat33 (Seppic) - PQ-33 + other |
| 34 | Poly(diethyliminio-1,3-propanediyldimethyliminio-1,3-propanediyl dibromide) | Mexomere PAK (Chimex) |
| 35 | Ethanaminium, N-carboxymethyl-N,N-dimethyl-2-(2-methyl-1-oxo-2-propenyloxy)-, inner salt, polymer with N,N,N-trimethyl-2-(2-methyl-1-oxo-2-propenyloxy)ethanaminium methyl sulfate | Plex 3074 L (Rohm GmbH) |
| 37 | N,N,N-Trimethyl-2-[(Methyl-1-Oxo-2-Propenyl)Oxy] Ethanaminium Chloride, Homopolymer | ULTRAGEL ® 300 (Cognis), SYNTHALEN® CN, CR, CU (3V Group), SYNTRAN ® PC 5320 (Interpolymer) |
| 42 | Poly [oxyethylene(dimethyliminio)ethylene (dimethylimino)ethylene dichloride] | Busan 1507 (Buckman Labs) |
| 44 | Poly(2-oxopyrrolidin-1-ylethylene, 3-methylimidazolium-1-ylethylene methyl sulfate) | Luviquat Ultracare, MS 370 (BAS F), SOFTENOL ® PQ44 (Zdchimmer & Schwarz Italianat S.p.A) |
| 45 | Glycine, N-methyl-N-[2-[(2-methyl-1-oxo-2-propenyl)oxy]ethyl]-, polymer with 2- | Plex 3073L (Rohm GmbH) |

TABLE 1-continued

| PQ | Description | Trade Name |
|----|-------------|------------|
|    | (dimethylamino)ethyl-2-methyl-2-propenoate, compound with dimethyl sulfate | |
| 46 | 1H-Imidazolium, 1-Ethenyl-3-Methyl-, Methyl Sulfate, Polymer with 1-Ethenylhexahydro-2H-Azepin-2-one and 1-Ethenyl-2-Pyrrolildinone | Luviquat Hold |
| 47 | 1-Propanaminium, N,N,N-Trimethyl-3-((2-Methyl-1-Oxo-2-Propenyl)Amino)-, Chloride, Polymer with Methyl 2-Propenoate and 2-Propenoic Acid | MERQUAT ® 2001, 2001N |
| 48 | Polymeric quaternary ammonium salt of formed from methacryloyl ethyl betaine, 2-hydroxyethyl methacrylate and methacryloyl ethyl trimethyl ammonium chloride | PLASCIZE ® L-450 (Goo Chemical) |
| 49 | Polymeric quaternary ammonium salt formed by the reaction of methacryloyl ethyl betaine, PEG-9 methacrylate and methacryloyl ethyl trimethyl ammonium chloride | PLASCIZER L-440 (Goo Chemical) |
| 50 | Carboxylatoethyldimethylammonioethyl 2-methyl-2-propenoate homopolymer | PLASCIZE ® L-401 (Goo Chemical) |
| 55 | 1-Dodecanaminium, N,N-Dimethyl-N-[3-[(2-Methyl-1-Oxo-2-Propenyl)-AminoPropyl]-, Chloride, Polymer with N-[3-(Dimethylamino)Propyl]-2-Methyl-2-Propenamide and 1-Ethenyl-2-Pyrrolidinone | Styreze W |
| 56 | 5-Isocyanato-1-(isocyanatomethyl)-1,3,3-trimethylcyclohexane, polymer with 1,3-butanediol and bis (2-hydroxyethyl) dimethylammonium methyl sulfate | Hairrol UC-4 (Sanyo Chemical) |
| 57 | 12-Hydroxy-9(Z)octadecenamidopropyltrimethylammonium chloride, polymers with ricinus communis (castor) oil, isooctdecanoic acid and butandioic acid | ZENIGLOSS ® Q (Zenitech) |
| 59 | Poly (20,25-dioxo-2,5,10,15,18-pentamethyl-10-(2-hydroxy-3-(3-phenyl-2-propenamido)propyldimethylammonio) propyl)-10-azonia-1,4,7,13,16,19-hexaoxapentacosanediyl)chloride | Crodasorb UV-HPP (Croda, Inc.) - PQ-59 and Butylene Glycol |
| 60 | 9-Octadecenoic Acid, 12-Hydroxy-, [(2-Hydroxyethyl)-Imino]Di-2,1-Ethanediyl Ester, Polymer with 5-Isocyanato-1-(Isocyanatomethyl)-1,3,3-Trimethylcyclohexane, Compd. with Diethyl Sulfate | Polylipid PPI-RC (Alzo/Bernel) - PQ-60 and Propylene Glycol |
| 61 | 2-Methyl-2-propenoyloxyethyl N,N,N-trimethylammonioethyl phosphate inner salt, polymer with octadecyl 2-methyl-2-propenoate | LIPIDURE ®-S (NOF) |
| 62 | Polymeric quaternary ammonium salt of butyl methacrylate, polyethylene glycol methyl ether methacrylate, ethylene glycol dimethacrylate and 2-methacryloylethyl trimonium chloride with 2,2'-azobis(2-methyl propionamidine)dihydrochloride | Nanoaquasome (Amore Pacific/Kyung-do) |
| 64 | 2-Methyl-2-propenoyloxyethyl N,N,N-trimethylammonio-ethyl phosphate inner salt, polymer with 2-hydroxy-3-(2-methyl-2-propenoyl)oxypropyltrimethylammonium chloride | LIPIDURE ®-C (NOF) |
| 67 | 2-Hydroxyethyl cellulose ether, reaction products with N,N,N-trimethyl-N-oxiranylmethylammonium chloride and N-dodecyl-N,N-dimethyl-N-oxiranylmethylammonium chloride | SOFTCAT ® (DOW Chemical) |
| 68 | 1-Ethenyl-2-pyrrolidinone, polymer with 1-ethenylimidazole and 1-ethenyl-3-methylimidazolium methyl sulfate | Luviquat Supreme |
| 69 | Polymeric quaternary ammonium salt composed of vinyl caprolactam, vinylpyrrolidone, dimethylaminopropyl methacrylamide (DMAPA), and methacryloylaminopropyl lauryldimonium chloride | AQUASTYLE ® 100, 300 (ISP) |

TABLE 1-continued

| PQ | Description | Trade Name |
|---|---|---|
| 71 | | ColaMoist 300P (Colonial Chemical Inc) |
| 72 | Polymeric quaternary ammonium salt of hydroxethylcellulose reacted with a coco-alkyl dimethyl ammonium substituted epoxide | MIRUSTYLE ® CP (Croda) |
| 73 | Polymeric quaternary ammonium salt consisting of propyltrimonium chloride acrylamide, ethyltrimonium chloride methacrylate and dimethylacrylamide monomers; Propanaminium, N,N,N-trimethyl-3-(2-propenamido)-, chloride, polymer with N,N,N-trimethyl-2-(2-methyl-2-propenoyloxy)ethanaminium chloride and N,N-dimethyl-2-propenamide | DIAFORMER ® C-802, C-823 (Mitsubishi Chem), DIASLEEK ® C-802, C-823 (Mitsubishi Chem) |
| 74 | | MIRAPOL ® PB 20 (Rhodia) Polycare Boost (Rhodia) |
| 75 | O-(2-Hydroxy-2-trimethylammoniopropyl)starch chloride, reaction products with O-(3-dodecyldimethylammonio-2-hydroxypropyl) starch chloride | Amylomer Cat 220EMU (Grafe Chemie) |
| 77 | Cocoglucoside Crosspolymer Hydroxypropyltrimonium Chloride | Colonial Poly SugaQuat TM-8610P (Colonial Chemical Inc) |
| 78 | Decylglucoside Crosspolymer Hydroxypropyl Laurdimonium Chloride | Colonial Poly SugaQuat L 1010P (Colonial Chemical Inc) |
| 79 | Decylglucoside Crosspolymer Hydroxypropyl Steardimonium Chloride | Colonial Poly SugaQuat SChloride 1010P (Colonial Chemical Inc) |
| 80 | Laurylglucoside Crosspolymer Hydroxypropyl Laurdimonium Chloride | Colonial Poly SugaQuat L-1210P (Colonial Chemical Inc.) |
| 81 | Laurylglucoside Crosspolymer Hydroxypropyl Steardimonium Chloride | Colonial Poly SugaQuat S 1210P (Colonial Chemical Inc) |
| 82 | Laurylglucoside Crosspolymer Hydroxypropyltrimonium Chloride | Colonial Poly SugaQuat TM-1218P (Colonial Chemical Inc) |
| 84 | Polymeric quaternary ammonium salt of acrylamidopropyltrimethylammonium chloride, trimethylaminoethyl methacrylate, dimethylacrylamide and hydroxyethylmethacrylate | DIASLEEK ® C-824 (Mitsubishi Chemical) |
| 85 | Polymeric quaternary ammonium salt of acrylamidopropyltrimethylammonium chloride, dimethylacrylamide and hydroxyethylmethacrylate | DIASLEEK ® C-825 (Mitsubishi Chemical) |
| 87 | Polymeric quaternary ammonium salt of vinylpyrrolidone, vinylimidazole and diallyldimethyl ammonium chloride | Luviquat Sensation (BASF) |
| 88 | Poly(Dilinoleyldimonium hydroxypropyl)chlorides) | ColaQuat PDQ (Colonial Chemical Inc) |
| 90 | Polymeric quaternary ammonium salt of acrylamide and hydroxyethylcellulose quaternized with diallyldimethyl ammonium chloride | Hymoquat AK325R (Hymo Corporation) |
| 91 | Polymeric quaternary ammonium salt of hydroxypropyl methacrylate and polyethylene glycol methacrylate quaternized with ethyltrimonium chloride methacrylate | SYNTRAN ® 5500 (Interpolymer) - PQ-91 and PA |
| 92 | Glycerylamidoethyl Methacrylate/Stearyl Methacrylate Copolymer | CERACUTE ®-G (NOF) |
| 101 | | DEPOSILK ® Q1 (Air Products) |

Preferred cationic polymers include a hydroxylethyl cellulose dimethyl diallylammonium chloride copolymer (PQ-4), a copolymer of acrylamide and diallyldimethylammonium chloride (PQ-7), a terpolymer of acrylic acid, methacrylamidopropyl trimethylammonium chloride, and methyl acrylate (PQ-47), and combinations thereof.

Microcapsules. Microcapsules can be prepared following encapsulation procedures known in the art. See for example U.S. Pat. Nos. 2,800,457, 3,870,542, 3,516,941, 3,415,758, 3,041,288, 5,112,688, 6,329,057, and 6,261,483.

One class of microcapsules contains a microcapsule wall encapsulating a microcapsule core wherein the microcapsule wall is formed of an encapsulating polymer and the microcapsule core contains an active material. Another type of microcapsules are the so-called reloadable microcapsules wherein the microcapsule core contains a sacrifice solvent and is free of an active material.

Wall forming materials (i.e., encapsulating polymers) include a melamine formaldehyde, polyurethane, polysiloxanes, polyurea, polyamide, polyimide, polyvinyl alcohol, polyanhydride, polyolefin, polysulfone, polysaccharide, protein, polypeptide, polylactide (PLA), polyglycolide (PGA), polyorthoester, polyphosphazene, silicone, lipid, modified cellulose, gum, polystyrene, polyester, polyether, and combination of these materials. Other polymeric materials that are functional are ethylene maleic anhydride copolymer, styrene maleic anhydride copolymer, ethylene vinyl acetate copolymer, and lactide glycolide copolymer. Biopolymers that are derived from alginate, chitosan, collagen, dextran, gelatin, and starch can also be used as the encapsulating materials. Additionally, capsules can be made via the simple or complex coacervation of gelatin. Preferred encapsulating wall polymers include those formed from isocyanates, acrylates, acrylamide, acrylate-co-acrylamide, hydrogel monomers, sol-gel precursors, gelatin, melamine-formaldehyde or urea-formaldehyde condensates, as well as similar types of aminoplasts.

Certain specific microcapsules and encapsulating polymers are described below as non-limiting examples.

1.1 Polyurea/Polyurethane Capsules. Polyurea capsules each have a microcapsule wall formed of an encapsulating polymer that is the polymerization reaction product of a polyisocyanate and a polyamine/polyalcohol. See WO 2004/054362; EP 0 148149; EP 0 017 409 B1; U.S. Pat. Nos. 4,417,916, 4,124,526, 4,285,720, 4,681,806, 5,583,090, 6,340,653 6, 566, 306, 6,730,635, 8,299,011, WO 90/08468, and WO 92/13450. In addition, the encapsulating polymer can also be prepared using a carbonyl crosslinker and a polyamine/polyalcohol.

1.1.1 Polyisocyanates. The polyisocyanates each contain two or more isocyanate (—NCO) groups. Suitable polyisocyanates include, for example, 1,5-naphthylene diisocyanate, 4,4'-diphenylmethane diisocyanate (MDI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), optionally in a mixture, 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, 4,4'-diisocyanatophenylperfluoroethane, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, and 3,3-bischloromethyl ether 4,4'-diphenyldiisocyanate. Sulfur-containing polyisocyanates are obtained, for example, by reacting hexamethylene diisocyanate with thiodiglycol or dihydroxydihexyl sulfide. Further suitable diisocyanates are trimethylhexamethylene diisocyanate, 1,4-diisocyanatobutane, 1,2-diisocyanatododecane, dimer fatty acid diisocyanate, and combinations thereof.

Other suitable commercially-available polyisocyanates include LUPRANATE® M20 (PMDI, commercially available from BASF containing isocyanate group "NCO" 31.5 wt %), where the average n is 0.7; PAPI 27 (PMDI commercially available from Dow Chemical having an average molecular weight of 340 and containing NCO 31.4 wt %) where the average n is 0.7; MONDUR® MR (PMDI containing NCO at 31 wt % or greater, commercially available from Bayer) where the average n is 0.8; MONDUR® MR Light (PMDI containing NCO 31.8 wt %, commercially available from Bayer) where the average n is 0.8; MONDUR® 489 (PMDI commercially available from Bayer containing NCO 30-31.4 wt %) where the average n is 1.0; poly[(phenylisocyanate)-co-formaldehyde](Aldrich Chemical, Milwaukee, WI), other isocyanate monomers such as DESMODUR® N3200 (poly(hexamethylene diisocyanate) commercially available from Bayer), and TAKENATE® D110-N (xylene diisocyanate adduct polymer commercially available from Mitsui Chemicals corporation, Rye Brook, NY, containing NCO 11.5 wt %), DESMODUR® L75 (a polyisocyanate base on toluene diisocyanate commercially available from Bayer), and DESMODUR® IL (another polyisocyanate based on toluene diisocyanate commercially available from Bayer).

In some embodiments, the polyisocyanate used in the preparation of the capsules of this invention is a single polyisocyanate. In other embodiments the polyisocyanate is a mixture of polyisocyanates. In some embodiments, the mixture of polyisocyanates includes an aliphatic polyisocyanate and an aromatic polyisocyanate. In particular embodiments, the mixture of polyisocyanates is a biuret of hexamethylene diisocyanate and a trimethylol propane-adduct of xylylene diisocyanate. In certain embodiments, the polyisocyanate is an aliphatic isocyanate or a mixture of aliphatic isocyanate, free of any aromatic isocyanate. In other words, in these embodiments, no aromatic isocyanate is used to prepare the polyurea/polyurethane polymers as capsule wall materials.

The average molecular weight of certain suitable polyisocyanates varies from 250 to 1000 Da and preferable from 275 to 500 Da. In general, the range of the polyisocyanate concentration varies from 0.1% to 10%, preferably from 0.1% to 8%, more preferably from 0.2 to 5%, and even more preferably from 1.5% to 3.5%, all based on the weight of the capsule delivery system.

More examples of suitable polyisocyanates can be found in WO 2004/054362; WO 2015/023961; EP 0 148149; EP 0 017 409 B1; U.S. Pat. Nos. 4,417,916, 4,124,526, 5,583,090, 6,566,306, 6,730,635, PCT 90/08468, PCT WO 92/13450, U.S. Pat. Nos. 4,681,806, 4,285,720 and 6,340,653.

1.1.2 Carbonyl Crosslinker. The carbonyl crosslinkers each have at least two functional groups, e.g., a first functional group and a second functional group.

The first functional group is an electrophilic group reactive towards the polyfunctional amine or the polyfunctional alcohol to form a network of the encapsulating polymer.

Examples include formyl, keto, carboxyl, a carboxylate ester group, an acyl halide group, an amide group, a carboxylic anhydride group, an alkyl halide group, an epoxide group, an aziridine group, an oxetane group, an azetidine group, a sulfonyl halide group, a chlorophosphate group, an isocyanate group, an α,β-unsaturated carbonyl group, an α,β-unsaturated nitrile group, or an α,β-unsaturated methanesulfonyl group. Preferably, the first function group is a carbonyl electrophilic group containing a carbonyl group such as formyl, keto, carboxyl, a carboxylate ester group, an acyl halide group, an amide group, a carboxylic anhydride group, an α,β-unsaturated carbonyl group, a trifluoromethanesulfonate group, and a p-toluenesulfonate group.

The second functional group is an electrophilic group reactive towards the polyfunctional amine or the polyfunctional alcohol. It can be selected from the groups listed immediately above.

Examples of a carbonyl crosslinker include glutaric dialdehyde, succinic dialdehyde, and glyoxal; as well as compounds such as glyoxyl trimer and paraformaldehyde, bis(dimethyl) acetal, bis(diethyl) acetal, polymeric dialdehydes, such as oxidized starch. Preferably the crosslinking agent is a low molecular weight, difunctional aldehyde, such as glyoxal, 1,3-propane dialdehyde, 1,4-butane dialdehyde, 1,5-pentane dialdehyde, or 1,6-hexane.

1.1.3 Polyfunctional Amines. Suitable polyfunctional amines include those described in WO 2015/023961. Examples are hexamethylenediamine, hexaethylenediamine, ethylenediamine, 1,3-diaminopropane, 1,4-diaminobutane, diethylenetriamine, pentaethylenehexamine, bis(3-aminopropyl)amine, bis(hexamethylene)triamine, tris(2-aminoethyl)amine, triethylene-tetramine, N,N'-bis(3-aminopropyl)-1,3-propanediamine, tetraethylenepentamine, amino-2-methyl-1-propanol, chitosan, 1,3-diamino-guanidine, 1,1-dimethylbiguanide, guanidine, arginine, lysine, histidine, ornithine, nisin, gelatin, and combinations thereof.

Other suitable polyamines include polyethylenimine and branched polyethylenimine ("BPEI"). Representative BPEI structure is shown below:

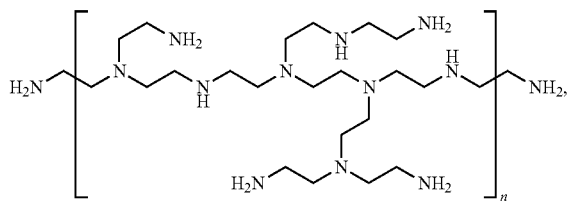

in which n is an integer from 1 to 20,000 (e.g., 1 to 10,000, 2 to 5,000, and 2 to 1,000). BPEI for use in this invention preferably has a molecular weight of 500 to 5,000,000 Daltons (e.g., 500 to 1,000,000 Daltons, 750 to 500,000 Daltons, 750 to 100,000 Daltons, and 750 to 50,000 Daltons).

BPEI are commercially available from Sigma-Aldrich (St. Louis, MO; average molecular weight 25,000 Daltons) and Polysciences Inc. (Warrington, PA; various products having molecular weight of 600, 1200, 1800, 10,000, 70,000, 750,000, 250,000, and 2,000,000 Daltons).

1.1.4 Polyfunctional Alcohols. Suitable polyfunctional alcohols are also described in WO 2015/023961. Examples include pentaerythritol, dipentaerythritol, glycerol, polyglycerol, ethylene glycol, polyethylene glycol, trimethylolpropane, neopentyl glycol, sorbitol, erythritol, threitol, arabitol, xylitol, ribitol, mannitol, galactitol, fucitol, iditol, inositol, volemitol, isomalt, maltitol, lactitol, maltotriitol, maltotetraitol, polyglycitol, and combinations thereof.

1.2 Aminoplast and Gelatin Microcapsules. A representative process used for aminoplast encapsulation is disclosed in U.S. Pat. No. 3,516,941, though it is recognized that many variations with regard to materials and process steps are possible. Another encapsulation process, i.e., gelatin encapsulation, is disclosed in U.S. Pat. No. 2,800,457. Both processes are discussed in the context of fragrance encapsulation for use in consumer products in U.S. Pat. Nos. 4,145,184 and 5,112,688, respectively. Polymer systems are well-known in the art and non-limiting examples of these include aminoplast capsules and encapsulated particles as disclosed in Application GB 2006709 A; the production of micro-capsules having walls comprising styrene-maleic anhydride reacted with melamine-formaldehyde precondensates as disclosed in U.S. Pat. No. 4,396,670; an acrylic acid-acrylamide copolymer, cross-linked with a melamine-formaldehyde resin as disclosed in U.S. Pat. No. 5,089,339; capsules composed of cationic melamine-formaldehyde condensates as disclosed in U.S. Pat. No. 5,401,577; melamine formaldehyde microencapsulation as disclosed in U.S. Pat. No. 3,074,845; amido-aldehyde resin in-situ polymerized capsules (see EP 0 158 449 A1); etherified urea-formaldehyde polymers (see U.S. Pat. No. 5,204,185); melamine-formaldehyde microcapsules as described in U.S. Pat. No. 4,525,520; cross-linked oil-soluble melamine-formaldehyde precondensates as described in U.S. Pat. No. 5,011,634; capsule wall material formed from a complex of cationic and anionic melamine-formaldehyde precondensates that are then cross-linked as disclosed in U.S. Pat. No. 5,013,473; polymeric shells made from addition polymers such as condensation polymers, phenolic aldehydes, urea aldehydes or acrylic polymers as disclosed in U.S. Pat. No. 3,516,941; urea-formaldehyde capsules as disclosed in EP 0 443 428 A2; melamine-formaldehyde chemistry as disclosed in GB 2 062 570 A; and capsules composed of polymer or copolymer of styrene sulfonic acid in acid of salt form, and capsules cross-linked with melamine-formaldehyde as disclosed in U.S. Pat. No. 4,001,140.

Urea-formaldehyde and melamine-formaldehyde precondensate microcapsule shell wall precursors are prepared by means of reacting urea or melamine with formaldehyde where the mole ratio of melamine or urea to formaldehyde is in the range of from about 10:1 to about 1:6, preferably from about 1:2 to about 1:5. For purposes of practicing this invention, the resulting material has a molecular weight in the range of from 156 to 3000. The resulting material may be used 'as-is' as a cross-linking agent for the aforementioned substituted or un-substituted acrylic acid polymer or copolymer or it may be further reacted with a $C_1$-$C_6$ alcohol, e.g., methanol, ethanol, 2-propanol, 3-propanol, 1-butanol, 1-pentanol or 1-hexanol, thereby forming a partial ether where the mole ratio of melamine/urea:formaldehyde:alcohol is in the range of 1:(0.1-6):(0.1-6). The resulting ether moiety-containing product may be used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or co-polymers. Methods for formation of such melamine-formaldehyde and urea-formaldehyde pre-condensates are set forth in U.S. Pat. Nos. 3,516,846 and 6,261,483, and Lee et al. (2002) *J. Microencapsulation* 19:559-569.

Examples of urea-formaldehyde pre-condensates useful in the practice of this invention are URAC 180 and URAC 186, available from Cytec Technology Corp. of Wilmington, DE. Examples of melamine-formaldehyde pre-condensates useful in the practice if this invention, include, but are not limited to, CYMEL® U-60, CYMEL® U-64 and CYMEL® U-65, trademarks of Cytec Technology Corp. of Wilmington, DE. It is preferable to use, as the precondensate for cross-linking, the substituted or un-substituted acrylic acid polymer or co-polymer. In practicing this invention, the range of mole ratios of urea-formaldehyde precondensate/melamine-formaldehyde pre-condensate to substituted/un-substituted acrylic acid polymer/co-polymer is in the range of from about 9:1 to about 1:9, preferably from about 5:1 to about 1:5 and most preferably from about 2:1 to about 1:2.

In one embodiment, microcapsules with polymer(s) composed of primary and/or secondary amine reactive groups or mixtures thereof and cross-linkers can also be used. See US 2006/0248665. The amine polymers can possess primary and/or secondary amine functionalities and can be of either natural or synthetic origin. Amine-containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable amine polymers are the LUPAMIN® series of polyvinyl formamides available from BASF. The molecular weights of these materials can range from 10,000 to 1,000,000 Daltons.

Urea-formaldehyde or melamine-formaldehyde capsules can also include formaldehyde scavengers, which are capable of binding free formaldehyde. When the capsules are for use in aqueous media, formaldehyde scavengers such as sodium sulfite, melamine, glycine, and carbohydrazine are suitable. When the capsules are aimed to be used in products having low pH, e.g., fabric care conditioners, formaldehyde scavengers are preferably selected from beta diketones, such as beta-ketoesters, or from 1,3-diols, such as propylene glycol. Preferred beta-ketoesters include alkylmalonates, alkyl aceto acetates and polyvinyl alcohol aceto acetates.

1.3 Sol-Gel Microcapsules. Sol-gel microcapsules each have a sol-gel polymer as the encapsulating polymer. The sol-gel polymer is the polymerization product of a sol-gel precursor, a compound capable of forming a sol-gel polymer. The sol-gel precursors are typically those containing silicon, boron, aluminum, titanium, zinc, zirconium, and vanadium. Preferred precursors are organosilicon, organoboron, organoaluminum including metal alkoxides and b-diketonates, and combinations thereof.

Sol-gel precursors suitable for the purposes of the invention are selected in particular from the group of di-, tri- and/or tetrafunctional silicic acids (including derivatives such as silicates), boric acids (including derivatives such as esters), and alumoesters, more particularly alkoxysilanes (alkyl orthosilicates), and precursors thereof.

One example of sol-gel precursors suitable for the purposes of the invention are compounds corresponding to the following general formula:

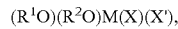

(R¹O)(R²O)M(X)(X'), wherein X can be hydrogen, —OR³, or R⁴; X' can be hydrogen, —OR⁵, or R⁶; and each of R¹, R², R³, R⁴, R⁵, R⁶ independently represent an organic group, more particularly a linear or branched alkyl group, preferably a $C_1$-$C_{12}$ alkyl. M can be Si, Ti, or Zr.

A preferred sol/gel precursor is alkoxysilanes corresponding to the following general formula: (R¹O) (R²O) Si (X) (X'), wherein each of X, X', R¹, and R² are defined above.

Particularly preferred compounds are the silicic acid esters such as tetramethyl orthosilicate (TMOS) and tetraethyl orthosilicate (TEOS). A preferred compound includes DYNASYLAN® (organofunctional silanes commercially available from Degussa Corporation, Parsippany, NJ, USA). Other sol-gel precursors suitable for the purposes of the invention are described, for example, in German Patent Application DE10021165. These sol-gel precursors are various hydrolyzable organosilanes such as, for example, alkylsilanes, alkoxysilanes, alkyl alkoxysilanes and organoalkoxysilanes. Besides the alkyl and alkoxy groups, other organic groups (for example allyl groups, aminoalkyl groups, hydroxyalkyl groups, etc.) may be attached as substituents to the silicon.

Recognizing that metal and semi metal alkoxide monomers (and their partially hydrolyzed and condensed polymers) such as tetramethoxy silane (TMOS), tetraethoxy silane (TEOS), etc. are very good solvents for numerous molecules and active ingredients is highly advantageous since it facilitates dissolving the active materials at a high concentration and thus a high loading in the final capsules.

Another class of sol-gel precursors are partially cross-linked silica, which is an oligomeric or polymeric silica having one or more (e.g., two or more) silicic acid functional groups such as silicic acid esters and alkoxysilane groups. Having these silicic acid functional groups, the partially crosslinked silica is capable of polymerizing with another sol-gel precursor and/or another partially crosslinked silica to form a sol-gel polymer, the microcapsule wall material that encapsulates an active material.

The partially crosslinked silica typically has a molecular weight less than 20,000 Da (e.g., 1,000 to 10,000 Da, 1,500 to 5,000 Da, and 2,000 to 3,500 Da).

The partially crosslinked silica can be prepared using an alkoxysilane described above. The alkoxysilane is polymerized to form oligomeric or polymeric silica having a molecular weight less than 20,000 Da. These partially crosslinked silica can then further polymerized to form a much larger sol-gel polymer to encapsulate an active material.

1.4 Hydrogel Microcapsules. Hydrogel microcapsules are prepared using a polymerizable material such as a monofunctional or multifunctional acrylic or methacrylic acid, or ester thereof. See e.g., WO2014/011860. Exemplary materials useful for preparing hydrogel microcapsules are listed below.

1.4.1 Monomers. Preferred bi- or polyfunctional vinyl monomers include by way of illustration and not limitation, acrylic acid, methacrylic acid, 2-hydroxyethyl acrylate, methyl acrylate, ethyl acrylate, propyl acrylate, n-butyl acrylate, pentyl acrylate, hexyl acrylate, 2-ethylhexyl acrylate, heptyl acrylate, octyl acrylate, nonyl acrylate, decyl acrylate, dodecyl acrylate, tetradecyl acrylate, hexadecyl acrylate, isopropyl acrylate, isobutyl acrylate, sec-butyl acrylate, 2-ethylbutyl acrylate, 3-methylbutyl acrylate, 1-ethylpropyl acrylate, 2-methylpentyl acrylate, 2-ethylbutyl acrylate, 1,3-dimethylbutyl acrylate, 1-methylbexyl acrylate, 2-ethylhexyl acrylate, 1-methylheptyl acrylate, 4-ethyl-1-methyloctyl acrylate, 4-ethyl-1,1-isobutyloctyl acrylate, allyl acrylate, 2-methylallyl acrylate, 1-methylallyl acrylate, 2-butenyl acrylate, 1,3-dimethyl-3-dibutenyl acrylate, 3,7-dimethyl-7-octenyl acrylate, 3,7-dimethyl-2,6-octadienyl acrylate, 3,7-dimethyl-6-octenyl acrylate, tert-butyl acrylate, triethylene glycol diacrylate, triethylene glycol dimethacrylate, diethylene glycol diacrylate, diethylene glycol dimethacrylate, tripropylene glycol diacrylate, aliphatic or aromatic urethane diacrylates, difunctional urethane acrylates, ethoxylated bisphenol diacrylate, ethoxylated bisphenol dimethylacrylate, ethoxylated aliphatic difunctional urethane methacrylates, ethoxylated trimethylolpropane triacrylate, ethoxylated pentaerythritol tetraacrylate, dipropylene glycol diacrylate, aliphatic or aromatic urethane dimethacrylates, epoxy acrylates, epoxymethacrylates, tetraethylene glycol dimethacrylate, tetraethylene glycol diacrylate, polyethylene glycol dimethacrylate, polyethylene glycol diacrylate, 1,3-butylene glycol diacrylate, 1,3-butylene glycol dimethacrylate, 1,4-butanediol dimethacrylate, 1,4-butaneidiol diacrylate, 1,6-hexanediol diacrylate, 1,6-hexanediol dimethacrylate, neopentyl glycol diacrylate, alkoxylated hexanediol diacrylate, alkoxylated cyclohexane dimethanol diacrylate, propoxylated neopentyl glycol diacrylate, trimethylolpropane trimethacrylate, trimethylolpropane triacrylate, pentaerythritol triacrylate, propoxylated trimethylolpropane triacrylate, propoxylated glyceryl triacrylate, ditrimethyloipropane tetraacrylate, dipentaerythritol pentaacrylate, and the like. Representative ester monomers of methacrylic acid, which can be used include 2-hydrox ethyl methacrylate, glycidyl methacrylate, methyl methacrylate, ethyl methacrylate, n-propyl methacrylate, isopropyl methacrylate, n-butyl methacrylate, isobutyl methacrylate, sec-butyl methacrylate, tert-butyl methacrylate, n-hexyl methacrylate, n-octyl methacrylate, isooctyl methacrylate, decyl methacrylate, n-dodecyl methacrylate, n-tetradecyl methacrylate, n-hexadecyl methacrylate, 2-ethylhexyl methacrylate, allyl methacrylate, oleyl methacrylate, 2-propynyl methacrylate, 2-(dimethylamino) ethyl methacrylate, 2-(diethylamino)ethyl methacrylate, 2-(diisopropylamino)ethyl methacrylate, N-(2-aminoethyl) methacrylamide hydrochloride, 2-aminoethyl methacrylate hydrochloride, N-(3-aminopropyl)methacrylamide hydrochloride, 2-(tert-butylamino)ethyl methacrylate, and the like.

The above monomers may be employed separately or in various mixtures. The use of multifunctional acrylate and methacrylate will lead to the formation of cross-linked network polymers upon polymerization. Such polymers have desirable properties such as good mechanical strength, elasticity, toughness, and flexibility. Examples of multifunctional acrylates and methacrylates of use in this invention include, but are not limited to, ethylene glycol dimethacrylate (EGDMA), trimethylolpropane trimethacrylate, trimethyloyl triacrylate, pentaerythritol triacrylate, pentaerythritol tetracrylate, bisphenol A dimethacrylate, di(trimethylolpropane) tetraacrylate (DTTA), 1-(acryloyloxy)-3-(methacryloyloxy)-2-propanol (AOOP), trimethylolpropane ethoxylate triacrylate (TPETA), dipentaerythritol pentaacrylate, hexane diacrylate, poly (ethylene glycol) dimethacrylate (PEGDMA), and 1,6-hexandiol dimethacrylate (HDDMA), 1,4-butandiol dimethacrylate, 1,3-butandiol dimethacrylate, 1,6-hexandiol diacrylate, 1,4-butandiol diacrylate, 1,3-butandiol diacrylate.

In certain embodiments, the acrylic or methacrylic acid, or ester thereof, makes up less than 25% by mass, preferably 5 to 20% by mass, or more preferably 10 to 15% by mass of the oil phase.

1.4.2 Initiators. Initiators are often used to start the polymerization reactions. Examples include but not limited to: AIBN, sodium persulfate, benzoyl peroxide.

1.5 Coascervate Capsules. Proteins useful in coacervation processes include albumins, vegetable globulins and gelatines. The gelatine may be fish, pork, beef, and/or poultry gelatine, for example. According to a preferred embodiment, the protein is fish, beef or poultry gelatine. According to a more preferred embodiment, the protein is warm water fish gelatine.

Typical non-protein polymers useful in complex coacervation methods include, in particular, negatively charged polymers. For example, they may be selected from gum arabic, xanthan, agar, alginate salts, cellulose derivatives, for example carboxymethyl cellulose, pectinate salts, carrageenan, polyacrylic and methacrylic acid, and/or mixtures thereof. Further suitable non-proteins can be derived from the literature, for example from to WO 2004/022221.

A cross-linking agent is typically used to harden the coating layer. Suitable cross-linking agents include formaldehyde, acetaldehyde, glutaraldehyde, glyoxal, chrome alum, or transglutaminase. Preferably, transglutaminase is used at 10-100, preferably 30-60 activity units per gram of gelatine. This enzyme is well described and commercially obtainable.

1.6 Microcapsule Formation Aids. Most microcapsule formation aids are used as dispersants (namely, emulsifiers or surfactants). They facilitate the formation of stable emulsions containing nano- or micro-sized oil drops to be encapsulated. Further, microcapsule formation aids improve the performance of the microcapsule by stabilizing capsules and/or their deposition to the target areas or releasing to the environment. Performance is measured by the intensity of the fragrance release during the use experience, such as the pre-rub and post-rub phases in a laundry experience. The pre-rub phase is the phase when the microcapsules have been deposited on the cloth, e.g., after a fabric softener containing microcapsules has been used during the wash cycle. The post-rub phase is after the microcapsules have been deposited and the microcapsules are broken by friction or other similar mechanisms.

The amount of these microcapsule formation aids is anywhere from about 0.1 to about 40 percent by weight of the microcapsule, more preferably from 0.5 to about 10 percent, more preferably 0.5 to 5 percent by weight.

Preferred microcapsule formation aids are polyvinyl pyrrolidone, polyvinyl alcohol, poly(styrene sulfonate), carboxymethyl cellulose, sodium salt of naphthalene sulfonate condensate, co-polymer of ethylene and maleic anhydride, an alginate, hyaluronic acid, poly(acrylic acid), carboxymethylcellulose, copolymers of acrylic acid and acrylamide, copolymer of acrylamide and acrylamidopropyltrimonium chloride, terpolymers of (acrylic acid, acrylamide, and acrylamidopropyltrimonium chloride), partially or completely hydrolyzed polyvinyl acetate polymers (i.e., polyvinyl alcohol), and combinations thereof.

Other microcapsule formation aids include water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, cellulose sulfate and pectin, isobutylene-maleic anhydride copolymer, carrageenan, sodium alginate, pectic acid, tragacanth gum, almond gum and agar; semi-synthetic polymers such as sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

Commercially available surfactants include, but are not limited to, sulfonated naphthalene-formaldehyde condensates such as MORWET® D425 (naphthalene sulfonate, Akzo Nobel, Fort Worth, TX); partially hydrolyzed polyvinyl alcohols such as MOWIOL®, e.g., MOWIOL® 3-83 (Air Products); ethylene oxide-propylene oxide block copolymers or poloxamers such as PLURONIC®, SYNPERONIC® or PLURACARE® materials (BASF); sulfonated polystyrenes such as FLEXAN® II (Akzo Nobel); ethylene-maleic anhydride polymers such as ZEMAC® (Vertellus Specialties Inc.); copolymer of acrylamide and acrylamidopropyltrimonium chloride such as SALCARE® SC 60 (BASF); and Polyquaternium series such as Polyquaternium 11 ("PQ11;" a copolymer of vinyl pyrrolidone and quaternized dimethylaminoethyl methacrylate; sold by BASF as LUVIQUAT PQ11 AT 1).

In other embodiments, the capsule formation aid is a processing aid such as hydrocolloids, which improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful in the present invention include, but are not limited to, polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly (alkyl(meth)acrylate-co-(meth)acrylic acid), poly(acrylic acid-co-maleic acid)copolymer, poly(alkyleneoxide), poly (vinylmethylether), poly(vinylether-co-maleic anhydride), and the like, as well as poly-(ethyleneimine), poly((meth) acrylamide), poly(alkyleneoxide-co-dimethylsiloxane), poly (amino dimethylsiloxane), and the like, and their quaternized forms.

The capsule formation aid may also be used in combination with carboxymethyl cellulose ("CMC"), polyvinylpyrrolidone, polyvinyl alcohol, sodium polystyrene sulfonate, alkylnaphthalenesulfonate formaldehyde condensates, and/or a surfactant during processing to facilitate capsule formation. Examples of surfactants that can be used in combination with the capsule formation aid include, but are not limited to, cetyl trimethyl ammonium chloride (CTAC), poloxamers such as PLURONIC® (e.g., PLURONIC® F127), PLURAFAC® (e.g., PLURAFAC® F127), or MIRANET-N, saponins such as Q-NATURALE® (National Starch Food Innovation); or a gum Arabic such as Seyal or Senegal. In certain embodiments, the CMC polymer has a molecular weight range between about 90,000 Daltons to 1,500,000 Daltons, preferably between about 250,000 Daltons to 750,000 Daltons and more preferably between 400,000 Daltons to 750,000 Daltons. The CMC polymer has a degree of substitution between about 0.1 to about 3, preferably between about 0.65 to about 1.4, and more preferably between about 0.8 to about 1.0. The CMC polymer is present in the capsule slurry at a level from about 0.1% to about 2% and preferably from about 0.3% to about 0.7%. in other embodiments, polyvinylpyrrolidone used in this invention is a water-soluble polymer and has a molecular weight of 1,000 to 10,000,000. Suitable polyvinylpyrrolidone are polyvinylpyrrolidone K12, K15, K17, K25, K30, K60, K90, or a mixture thereof. The amount of polyvinylpyrrolidone is 2-50%, 5-30%, or 10-25% by weight of the capsule delivery system. Commercially available alkylnaphthalenesulfonate formaldehyde condensates include MORWET® D-425, which is a sodium salt of naphthalene sulfonate condensate by Akzo Nobel, Fort Worth, TX.

In food products, food-grade dispersants are use. The term "food-grade dispersant" refers to a dispersant having a quality as fit for human consumption in food. They can be natural or non-natural products. A natural product or surfactant refers to a product that is naturally occurring and comes from a nature source. Natural products/surfactants include their derivatives which can be salted, desalted, deoiled, fractionated, or modified using a natural enzyme or microorganism. On the other hand, a non-natural surfactant is a chemically synthesized surfactant by a chemical process that does not involve an enzymatic modification.

Natural dispersants include quillaja saponin, lecithins, gum arabic, pectin, carrageenan, chitosan, chondroitin sulfate, cellulose gum, modified starch, whey protein, pea protein, egg white protein, silk protein, gelatin of fish, proteins of porcine or bovine origin, ester gum, fatty acids, and combinations thereof.

Non-natural dispersants include N-lauroyl-L-arginine ethyl ester, sorbitan esters, polyethoxylated sorbitan esters, polyglyceryl esters, fatty acid esters, and combination thereof.

Other food safe dispersant can also be included in the microcapsule of this invention. Examples include ammonium phosphatides, acetic acid esters of mono- and diglycerides (Acetem), lactic acid esters of mono- and diglycerides of fatty acids (Lactem), citric acid esters of mono and diglycerides of fatty acids (Citrem), mono and diacetyl tartaric acid esters of mono and diglycerides of fatty acids (Datem), succinic acid esters of monoglycerides of fatty acids (SMG), ethoxylated monoglycerides, sucrose esters of fatty acids, sucroglycerides, polyglycerol polyricinoleate, propane-1,2-diol esters of fatty acids, thermally oxidized soya bean oil interacted with mono- or diglycerides of fatty acids, sodium stearoyl lactylate (SSL), calcium stearoyl lactylate (CSL), stearyl tartrate, polyglycerol esters of interesterified castor oil acid (E476), sodium stearoyllatylate, sodium lauryl sulfate, polyoxyethylated hydrogenated castor oil (for instance, such sold under the trade name CREMOPHOR®), block copolymers of ethylene oxide and propylene oxide (for instance as sold under the trade name PLURONIC® or Poloxamer), polyoxyethylene fatty alcohol ethers, and polyoxyethylene stearic acid ester.

1.7 Additional Wall Polymer. The Encapsulating polymer can also include one or more additional wall polymers, e.g., a second, third, fourth, fifth, or sixth polymer. These additional polymers can be selected from the group consisting of silica, polyacrylate, polyacrylamide, poly(acrylate-co-acrylamide), polyurea, polyurethane, starch, gelatin and gum Arabic, poly(melamine-formaldehyde), poly(urea-formaldehyde), and combinations thereof.

1.8 Encapsulation Methods. Conventional encapsulation methods can be used to prepare the microcapsules. See WO 2015/023961.

By way of illustration, to prepare a microcapsule having a polyurea encapsulating polymer, an oil-in-water emulsion is first prepared containing (i) a polyamine, a polyalcohol, or mixture thereof, (ii) a polyisocyanate, carbonyl crosslinker, or mixture thereof, (iii) an oil phase having a hydrophilic core solvent and a hydrophobic core solvent, and (iv) an aqueous phase having a microcapsule formation aid and water. The reaction between the polyamine/polyalcohol and the polyisocyanate/carbonyl crosslinker occurs when the temperature of the reaction mixture is raised or a catalyst (such as a transglutaminase for catalyzing amide formation) is added to the mixture.

Catalysts suitable for use in the polyurea/polyurethane formation are transglutaminases, metal carbonates, metal hydroxide, amino or organometallic compounds and include, for example, sodium carbonate, cesium carbonate, potassium carbonate, lithium hydroxide, 1,4-diazabicyclo [2.2.2]octane (i.e., DABCO), N,N-dimethylaminoethanol, N,N-dimethylcyclohexylamine, bis-(2-dimethylaminoethyl) ether, N,N-dimethylacetylamine, stannous octoate and dibutyltin dilaurate.

The resultant microcapsule slurry is then cured at a predetermined temperature for a predetermined period of time.

In accordance with some embodiments, the microcapsules prepared according to the methods above are cured at a temperature in the range of, e.g., 15° C. to 230° C. (e.g., 55° C. to 90° C., 55° C. to 75° C., and 90° C. to 130° C.) for 1 minute to 10 hours (e.g., 0.1 hours to 5 hours, 0.2 hours to 4 hours and 0.5 hours to 3 hours). A skilled person in the art can determine, without undue experiments, the curing temperature, duration, and the heating rate.

To obtain microcapsules with more leaching of the active material, certain embodiments of this invention provide for a cure at a low temperature, e.g., less than 100° C. In some embodiments, the cure temperature is at or less than 90° C. In other embodiments, the cure temperature is at or less than 80° C.

In one embodiment, the capsules are heated to a target cure temperature at a linear rate of 0.5 to 2° C. per minute (e.g., 1 to 5° C. per minute, 2 to 8° C. per minute, and 2 to 10° C. per minute) over a period of 1 to 60 minutes (e.g., 1 to 30 minutes). The following heating methods may be used: conduction for example via oil, steam radiation via infrared, and microwave, convection via heated air, steam injection and other methods known by those skilled in the art. The target cure temperature used herein refers to the minimum temperature in degrees Celsius at which the capsules may be cured to retard leaching.

2. Active Materials. The microcapsule compositions of the invention have one or more active materials in the external hydrophilic solvent. Nonlimiting examples include those described in WO2015/023961.

The microcapsule compositions can also include the following active materials:

(i) taste masking agents, substances for masking one or more unpleasant taste sensations, in particular a bitter, astringent and/or metallic taste sensation or aftertaste. Examples include lactisol [2O-(4-methoxyphenyl) lactic acid](cf. U.S. Pat. No. 5,045,336), 2,4-dihydroxybenzoic acid potassium salt (cf. U.S. Pat. No. 5,643, 941), ginger extracts (cf. GB 2,380,936), neohesperidine dihydrochalcone (cf. Manufacturing Chemist 2000, July issue, p. 16-17), specific flavones (2-phenylchrom-2-en-4-ones) (cf. U.S. Pat. No. 5,580, 545), specific nucleotides, for example cytidine-5'-monophosphates (CMP) (cf. US 2002/0177576), specific sodium salts, such as sodium chloride, sodium citrate, sodium acetate and sodium lactate (cf. Nature, 1997, Vol. 387, p. 563), a lipoprotein of β-lactoglobulin and phosphatidic acid (cf. EPA 635 218), neodiosmine [5,7-dihydroxy-2-(4-methoxy-3-hydroxyphenyl)-7-O-neohesperidosyl-chrom-2-en-4-one] (cf. U.S. Pat. No. 4,154,862), preferably hydroxyflavanones according to EP 1 258 200, in turn preferred in this respect 2-(4-hydroxyphenyl)-5,7-dihydroxychroman-4-one (naringenin), 2-(3,4-dihydroxyphenyl)-5,7-dihydroxychroman-4-one (eriodictyol), 2-(3,4-dihydroxyphenyl)-5-hydroxy-7-methoxychroman-4-one (eriodictyol-7-methylether), 2-(3,4-dihydroxyphenyl)-7-hydroxy-5-methoxychroman-4-one (eriodictyol-5-methylether) and 2-(4-hydroxy-3-methoxyphenyl)-5,7-dihydroxychroman-4-one (homoeriodictyol), the (2S)- or (2R)-enantiomers thereof or mixtures thereof as well as the mono- or polyvalent phenolate salts thereof with $Na^+$, $K^+$, $NH4^+$, $Ca^{2+}$, $Mg^{2+}$ or $Al^+$ as counter cations or y-aminobutyric acid (4-aminobutyric acid, as the neutral form ("inner salt") or in the carboxylate or ammonium form) according to WO 2005/09684;

(ii) taste sensates including hot tasting, salivation-inducing substances, substances causing a warmth or tingling feeling, and cooling active ingredients. Examples of hot tasting and/or salivation-inducing substances and/or substances which cause a feeling of warmth and/or a tingling feeling on the skin or on the mucous membranes and which can be a constituent of the products according to the invention are: capsaicin, dihydrocapsaicin, gingerol, paradol, shogaol, piperine, carboxylic acid-N-vanillylamides, in particular nonanoic acid-N-vanillylamide, pellitorin or spilanthol, 2-nonanoic acid amides, in particular 2-nonanoic acid-N-isobutylamide, 2-nonanoic acid-N-4-hydroxy-3-methoxyphenylamide, alkyl ethers of 4-hydroxy-3-methoxybenzyl alcohol, in particular 4-hydroxy-3-methoxybenzyl-n-butylether, alkyl ethers of 4-acyloxy-3-methoxybenzyl alcohol, in particular 4-acetyloxy-3-methoxybenzyl-n-butylether and 4-acetyloxy-3-methoxybenzyl-n-hexylether, alkyl ethers of 3-hydroxy-4-methoxybenzyl alcohol, alkyl ethers of 3,4-dimethoxybenzyl alcohol, alkyl ethers of 3-ethoxy-4-hydroxybenzyl alcohol, alkyl ethers of 3,4-methylene dioxybenzyl alcohol, (4-hydroxy-3-methoxyphenyl)acetic acid amides, in particular (4-hydroxy-3-methoxyphenyl)acetic acid-N-n-octylamide, vanillomandelic acid alkylamides, ferulic acid-phenethylamides, nicotinaldehyde, methylnicotinate, propylnicotinate, 2-butoxyethylnicotinate, benzylnicotinate, 1-acetoxychavicol, polygodial and isodrimeninol, further preferred cis- and/or trans-pellitorin according to WO 2004/000787 or WO 2004/043906, alkenecarboxylic acid-N-alkylamides according to WO 2005/ 044778, mandelic acid alkylamides according to WO 03/106404 or alkyloxyalkanoic acid amides according to WO 2006/003210. Examples of preferred hot tasting natural extracts and/or natural extracts which cause a feeling of warmth and/or a tingling feeling on the skin or on the mucous membranes and which can be a constituent of the products according to the invention are: extracts of paprika, extracts of pepper (for example *capsicum* extract), extracts of chili pepper, extracts of ginger roots, extracts of *Aframomum melgueta*, extracts of s, extracts of *Kaempferia galangal* or extracts of

*Alpinia galanga*. Suitable cooling active ingredients include the following: 1-menthol, d-menthol, racemic menthol, menthone glycerol acetal (trade name: FRESCOLAT® MGA), menthyl lactate (trade name: FRESCOLAT® ML, menthyl lactate preferably being 1-menthyl lactate, in particular 1-menthyl-1-lactate), substituted menthyl-3-carboxamides (for example menthyl-3-carboxylic acid-N-ethylamide), 2-isopropyl-N-2,3-trimethyl-butanamide, substituted cyclohexane carboxamides, 3-menthoxypropane-1,2-diol, 2-hydroxyethyl menthyl carbonate, 2-hydroxypropyl menthyl carbonate, N-acetylglycine menthyl ester, isopulegol, hydroxycarboxylic acid menthyl esters (for example menthyl-3-hydroxybutyrate), monomenthyl succinate, 2-mercaptocyclodecanone, menthyl-2-pyrrolidin-5-onecarboxylate, 2,3-dihydroxy-p-menthane, 3,3,5-trimethylcyclohexanone glycerol ketal, 3-menthyl-3,6-di- and -trioxaalkanoates, 3-menthyl methoxyacetate and icilin. Cooling active ingredients which are particularly preferred are as follows: 1-menthol, racemic menthol, menthone glycerol acetal (trade name: FRESCOLAT® MGA), menthyl lactate (preferably 1-menthyl lactate, in particular 1-menthyl-1-lactate, trade name: FRESCOLAT® ML), 3-menthoxypropane-1,2-diol, 2-hydroxyethyl menthyl carbonate, 2-hydroxypropyl menthyl carbonate.

(iii) malodor counteracting agents including an α,β-unsaturated carbonyl compounds including but not limited to those disclosed in U.S. Pat. No. 6,610,648 and EP 2,524,704, amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, isomers of bicyclo[2.2.1]hept-5-ene-2-carboxylic acid, ethyl ester, nano silver, zinc undecenylate, β-naphthyl methyl ether, β-naphthyl ketone, benzyl acetone. They may include mixture of hexahydro-4,7-methanoinden-5-yl propionate and hexahydro-4,7-methanoinden-6-yl propionate; 4-(2,6,6-trimethyl-2-cyclohexen-1-yl)-3-methyl-3-buten-2-one; 3,7-dimethyl-2,6-nonadien-1-nitrile; dodecahydro-3a,6,6,9a-tetramethylnaphtho(2,1-b)furan; ethylene glycol cyclic ester of n-dodecanedioic acid; 1-cyclohexadecen-6-one; 1-cycloheptadecen-10-one; and corn mint oil. They may also include 1-cyclohexylethan-1-yl butyrate; 1-cyclohexylethan-1-yl acetate; 1-cyclohexylethan-1-ol; methylethyl)cyclohexylethan-1-yl propionate; and 2'-hydroxy-1'-ethyl(2-phenoxy)acetate each of which compound is marketed under the trademark VEILEX® by International Flavors & Fragrances Inc. More suitable malodor counteracting agents are polymers containing an α-keto, benzaldehyde, or α,β-unsaturated carbonyl moiety, such as those described in US Application Publications 2012/0294821, 2013/0101544 and 2013/0101545;

(iv) vitamins including any vitamin, a derivative thereof and a salt thereof. Examples are as follows: vitamin A and its analogs and derivatives (e.g., retinol, retinal, retinyl palmitate, retinoic acid, tretinoin, and isotretinoin, known collectively as retinoids), vitamin E (tocopherol and its derivatives), vitamin C (L-ascorbic acid and its esters and other derivatives), vitamin B3 (niacinamide and its derivatives), alpha hydroxy acids (such as glycolic acid, lactic acid, tartaric acid, malic acid, citric acid, etc.) and beta hydroxy acids (such as salicylic acid and the like);

(v) antibacterials including bisguanidines (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol), triclosan (i.e., 2,4,4'-trichloro-2'-hydroxy-diphenylether), thymol, and triclocarban;

(vi) sunscreen actives including oxybenzone, octylmethoxy cinnamate, butylmethoxy dibenzoylmethane, p-aminobenzoic acid and octyl dimethyl-p-aminobenzoic acid; (vii) antioxidants such as beta-carotene, vitamin C (Ascorbic Acid) or an ester thereof, vitamin A or an ester thereof, vitamin E or an ester thereof, lutein or an ester thereof, lignan, lycopene, selenium, flavonoids, vitamin-like antioxidants such as coenzyme Q10 (CoQ10) and glutathione, and antioxidant enzymes such as superoxide dismutase (SOD), catalase, and glutathione peroxidase;

(viii) anti-inflammatory agents including, e.g., methyl salicylate, aspirin, ibuprofen, and naproxen. Additional anti-inflammatories useful in topical applications include corticosteroids, such as, but not limited to, flurandrenolide, clobetasol propionate, halobetasol propionate, fluticasone propionate, betamethasone dipropionate, betamethasone benzoate, betamethasone valerate, desoximethasone, dexamethasone, diflorasone diacetate, mometasone furoate, amcinodine, halcinonide, fluocinonide, fluocinolone acetonide, desonide, triamcinolone acetonide, hydrocortisone, hydrocortisone acetate, fluoromethalone, methylprednisolone, and predinicarbate;

(ix) anesthetics that can be delivered locally including benzocaine, butamben, butamben picrate, cocaine, procaine, tetracaine, lidocaine and pramoxine hydrochloride;

(x) analgesics such as ibuprofen, diclofenac, capsaicin, and lidocaine;

(xi) antifungal agents. Non-limiting examples are micanazole, clotrimazole, butoconazole, fenticonasole, tioconazole, terconazole, sulconazole, fluconazole, haloprogin, ketonazole, ketoconazole, oxinazole, econazole, itraconazole, torbinafine, nystatin and griseofulvin;

(xii) antibiotics such as erythromycin, clindamycin, synthomycin, tetracycline, metronidazole and the like;

(xiii) anti-viral agents including famciclovir, valacyclovir and acyclovir;

(xiv) anti-parasitic agents such as scabicides, such as permethrin, crotamiton, lindane and ivermectin;

(xv) anti-infectious and anti-acne agents including benzoyl peroxide, sulfur, resorcinol and salicylic acid;

(xvi) dermatological active ingredients useful in topical applications including, e.g., jojoba oil and aromatic oils such as methyl salicylate, wintergreen, peppermint oil, bay oil, *eucalyptus* oil and citrus oils, as well as ammonium phenolsulfonate, bismuth subgallate, zinc phenolsulfonate and zinc salicylate;

(xvii) enzymes and co-enzymes useful for topical application including co-enzyme Q10, papain enzyme, lipases, proteases, superoxide dismutase, fibrinolysin, desoxyribonuclease, trypsin, collagenase and sutilains;

(xviii) skin whitening agents such as hydroquinone and monobenzone;

(xix) anti-histamines including chlorpheniramine, brompheniramine, dexchlorpheniramine, tripolidine, clemastine, diphenhydramine, prometazine, piperazines, piperidines, astemizole, loratadine and terfonadine;

(xx) chemotherapeutic agents such as 5-fluorouracil, masoprocol, mechlorethamine, cyclophosphamide, vincristine, chlorambucil, streptozocin, methotrexate, bleomycin, dactinomycin, daunorubicin, coxorubicin and tamoxifen;

(xxi) insect repellents including pediculicides for treatment of lice, such as pyrethrins, permethrin, malathion, lindane and the like;

(xxii) taste modulators including sweetness enhancer such as positive allosteric modulators (PAMs), bitterness inhibitors, saltiness enhancers, sourness inhibitors, and umami enhancers. Active materials also include flavor enhancer, taste modulators and artificial sweeteners. Exemplary sweetener and sweet modulators are rebaudioside C; plant extracts and derivatives, e.g., transglucosylated *R. suavissimus* extract; naringenin and salts; positive allosteric modulators ("PAMs") such as sulfamide compounds. See WO 2013/096290; US 2015/0305380; US 2015/0272184; and WO 2015/199987. Exemplary salt taste modulators include apsaicin; resiniferatoxin (RTX); piperine; 2-(3,4-dimethylbenzyl)-3-{[(4-hydroxy-3-methoxybenzyl)amino]carbothioyl}propyl pivalate (agonist 23); olvanil, capsiate; evodiamine; ethanol; cetylpyridinium chloride; dodecylpyridinium bromide; capsazepin; SB366791, etc. See WO 2005/006881;

(xxiii) sweeteners such as steviol glycosides (Stevioside, Rebaudioside A, Rebaudioside C, Dulcoside A, Rebaudioside B, Rebaudioside D, Rebaudioside E, rubusoside, and combinations thereof), carbohydrate sweetener (sucrose, lactose, trehalose, glucose, fructose, sorbitol, mannitol, lactitol, xylitol, inulin, oligofructose, fructooligosaccharides, corn syrup, fruit juice concentrate, honey, malt, rice syrup, molasses, and agave syrup), and other artificial sweeteners (aspartame, sucralose, neotame, acesulfame potassium (Ace-K), saccharin, and advantame);

(xxxiv) probiotics, namely live microorganisms which, when administered in effective amounts, confer a beneficial physiological effect on the host. Examples include *L. bulgaricus, S. thermophiles, B. bifidum, L. lactis* spp. *Lactis, B. infantis, B. longum, L. paracasei, L. acidophilus, B. lactis, L. casei, B. adolescentis, B. breve, L. rhamnosus*, and other *Lactobacillus* and *Bifidobacterium* genera.

In addition to the active materials listed above, the products of this invention can also contain, for example, the following dyes, colorants or pigments: lactoflavin (riboflavin), beta-carotene, riboflavin-5'-phosphate, alpha-carotene, gamma-carotene, cantaxanthin, erythrosine, curcumin, quinoline yellow, yellow orange S, tartrazine, bixin, norbixin (annatto, orlean), capsanthin, capsorubin, lycopene, beta-apo-8'-carotenal, beta-apo-8'-carotenic acid ethyl ester, xantophylls (flavoxanthin, lutein, cryptoxanthin, rubixanthin, violaxanthin, rodoxanthin), fast carmine (carminic acid, cochineal), azorubin, cochineal red A (Ponceau 4 R), beetroot red, betanin, anthocyanins, amaranth, patent blue V, indigotine I (indigo-carmine), chlorophylls, copper compounds of chlorophylls, acid brilliant green BS (lissamine green), brilliant black BN, vegetable carbon, titanium dioxide, iron oxides and hydroxides, calcium carbonate, aluminum, silver, gold, pigment rubine BK (lithol rubine BK), methyl violet B, victoria blue R, victoria blue B, acilan brilliant blue FFR (brilliant wool blue FFR), naphthol green B, acilan fast green 10 G (alkali fast green 10 G), ceres yellow GRN, sudan blue II, ultramarine, phthalocyanine blue, phthalocayanine green, fast acid violet R. Further naturally obtained extracts (for example paprika extract, black carrot extract, red cabbage extract) can be used for coloring purposes. Goods results are also achieved with the colors named in the following, the so-called aluminum lakes: FD & C Yellow 5 Lake, FD & C Blue 2 Lake, FD & C Blue 1 Lake, Tartrazine Lake, Quinoline Yellow Lake, FD & C Yellow 6 Lake, FD & C Red 40 Lake, Sunset Yellow Lake, Carmoisine Lake, Amaranth Lake, Ponceau 4R Lake, Erythrosyne Lake, Red 2G Lake, Allura Red Lake, Patent Blue V Lake, Indigo Carmine Lake, Brilliant Blue Lake, Brown HT Lake, Black PN Lake, Green S Lake and mixtures thereof.

In some embodiments, the amount of active material in the microcapsule composition is from 0.1 to 95% (e.g., 1 to 90%, 2% to 80%, 4 to 70%, and 5 to 50%) by weight of the composition. The amount of the capsule wall is from 10 to 98% (e.g., 20 to 95%, 30 to 90%, and 50 to 80%) by weight of the capsule. The amount of the microcapsule core (the sum of the hydrophilic and hydrophobic core solvents) is from 2 to 90% (e.g., 5 to 80%, 10 to 70%, and 20 to 50%) by weight of the capsule.

In some microcapsule compositions, the ratio between the capsule and active material is 4:1 to 40:1 (e.g., 5:1 to 30:1 and 6:1 to 20:1).

3. Adjunct Materials. The present invention also contemplates the incorporation of adjunct materials including emollients, and core modifier materials in the core encapsulated by the capsule wall. Other adjunct materials are solubility modifiers, density modifiers, stabilizers, viscosity modifiers, pH modifiers, or any combination thereof. These modifiers can be present in the wall or core of the capsules, or outside the capsules in the microcapsule compositions. Preferably, they are in the core as a core modifier.

The one or more adjunct material may be added in the amount of from 0.01% to 25% (e.g., from 0.5% to 10%) by weight of the capsule.

3.1 Emollients. Emollients have the quality of softening or soothing the skin. They keep the skin moist and flexible, helping to prevent cracks. Commonly used emollients are described below.

3.1.1 Triglycerides and modified triglycerides as emollients. These include vegetable oils such as jojoba, soybean, canola, sunflower, safflower, rice bran, avocado, almond, olive, sesame, persic, castor, coconut, and mink oils.

3.1.2 Ester oils have at least one ester group in the molecule. One type of common ester oil useful in the present invention are the fatty acid mono and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate.

3.1.3 Ester oil as a liquid polyester formed from the reaction of a dicarboxylic acid and a diol. Examples of polyesters suitable for the present invention are the polyesters marketed by ExxonMobil under the trade name PURESYN® ESTERS and Polyalphaolefins (PAO), hydrophobic plant extracts.

3.1.4 Silicones include, for example, linear and cyclic polydimethylsiloxanes, amino-modified, alkyl, aryl, and alkylaryl silicone oil.

3.1.5 Low/Non-Volatile Hydrocarbons
3.2 Solid Materials

Nanoscale solid particulate materials such as those disclosed in U.S. Pat. No. 7,833,960 may also be incorporated into the core and may be selected from, but not limited to, metal or metallic particles, metal alloys, polymer particles, wax particles, inorganic particulates, minerals and clay particles.

The metal particles can be selected from a non-limiting list of main group elements, transition metal and post-transition metal elements including aluminum (Al), silica (Si), Titanium (Ti), chromium (Cr), manganese (Mn), iron (Fe), nickel (Ni), cobalt (Co), copper (Cu), gold (Au), silver (Ag), platinum (Pt) and palladium (Pd).

Polymer particles of any chemical composition and nature are suitable for the present invention as long as their physical dimension falls into the prescribed region and a liquid core is generated. The polymer particles can be selected from a nonlimiting list of polymers and co-copolymer based on polystyrene, polyvinyl acetate, polylactides, polyglycolides, ethylene maleic anhydride copolymer, polyethylene, polypropylene, polyamide, polyimide, polycarbonate, polyester, polyurethane, polyurea, cellulose and cellulose, and combinations and mixture of such polymers.

The inorganic particulate can be selected from a non-limiting list including silica, titanium dioxide ($TiO_2$), zinc oxide (ZnO), $Fe_2O_3$, and other metal oxides such as but not limited to NiO, $Al_2O_3$, SnO, $SnO_2$, $CeO_2$, ZnO, CdO, $RuO_2$, FeO, CuO, AgO, $MnO_2$, as well as other transition metal oxides.

Examples of nanoscaled material include AEROSIL® R812, which has a particle size of less than 25 nm according to the specification from the manufacture, Degussa Corp. Other suitable materials from Degussa include, but not limited to, AEROSIL® R972, AEROSIL® R974, AEROSIL® R104, AEROSIL® R106, AEROSIL® R202, AEROSIL® R805, AEROSIL® R812, AEROSIL® R812S, AEROSIL® R816, AEROSIL® R7200, AEROSIL® R9200, and AEROXIDE® $TiO_2$ P25, AEROXIDE® T805, AEROXIDE® LE1, AEROXIDE® LE2, AEROXIDE® $TiO_2$ NKT 90, AEROXIDE® Alu C805, titanium dioxide PF2, SIPERNAT® D110, SIPERNAT® D-380. The hydrophobic materials from Deguassa Corp. such as including Aerosile R812 and R972 are especially preferred.

Nanoscaled materials such as UVINUL® $TiO_2$ and Z-COTE® HP1 manufactured by BASF can also be used as well as and TI-PURE® titanium dioxide, TI-PURE® R-700, and TI-SELECT. Additional suitable materials include TS-6200 from Dupont and Zerofree 516, Huberderm 2000 and Huberderm 1000 from the J.M. Huber Corporation, Havre De Grace, MD. Silica products such as SYLOID® 63, 244, 72, 63FP 244FP, 72FP, Sylox 15, 2 and Zeolites such as SYLOSIV® A3, SYLOSIV® A4 and SYLOSIV® K300 from Grace Davison can also be used.

3.3 Polymeric Core Modifiers. Polymeric core modifiers are also contemplated. It has been found that the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion. Polymeric core modifiers include copolymers of ethylene; copolymers of ethylene and vinyl acetate (EL-VAX® polymers by DOW Corporation); copolymers of ethylene and vinyl alcohol (EVAL® polymers by Kuraray); ethylene/acrylic elastomers such as Valnac polymers by Dupont; polyvinyl polymers, such as polyvinyl acetate; alkyl-substituted cellulose, such as ethyl cellulose (ETHOCEL® made by DOW Corporation) and hydroxypropyl celluloses (KLUCEL® polymers by Hercules); cellulose acetate butyrate available from Eastman Chemical; polyacrylates (e.g., AMPHOMER®, Demacryl LT and Dermacryl 79, made by National Starch and Chemical Company, the AMERHOLD polymers by Amerchol Corporation, and ACUDYNE® 258 by ISP Corporation); copolymers of acrylic or methacrylic acid and fatty esters of acrylic or methacrylic acid such as INTELIMER® polymers made by Landec Corporation (see also U.S. Pat. Nos. 4,830,855, 5,665,822, 5,783,302, 6,255,367 and 6,492,462); polypropylene oxide; polybutylene oxide of poly(tetrahydrofuran); polyethylene terephthalate; polyurethanes (Dynam X by National Starch); alkyl esters of poly(methyl vinyl ether); maleic anhydride copolymers, such as the GANTREZ® copolymers and OMNIREZ® 2000 by ISP Corporation; carboxylic acid esters of polyamines, e.g., ester-terminated polyamides (ETPA) made by Arizona Chemical Company; polyvinyl pyrrolidone (LUVISKOL® series of BASF); block copolymers of ethylene oxide, propylene oxide and/or butylenes oxide including, e.g., PLURONIC® and SYNPERONIC® polymers/dispersants by BASF. Another class of polymers include polyethylene oxide-co-propyleneoxide-co-butylene oxide polymers of any ethylene oxide/propylene oxide/butylene oxide ratio with cationic groups resulting in a net theoretical positive charge or equal to zero (amphoteric). The general structure is:

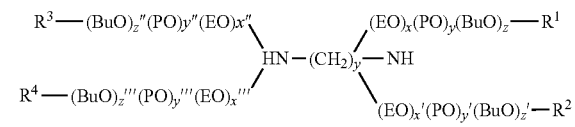

where $R^1$, $R^2$, $R^3$, and $R^4$ are independently H or any alkyl or fatty alkyl chain group. Examples of such polymers are the commercially known as TETRONIC® by BASF Corporation.

3.4 Solubility Modifiers. Nonlimiting examples of a solubility modifier include surfactants (e.g., SLS and TWEEN® 80), acidic compounds (e.g., mineral acids such as sulfuric acid, hydrochloric acid, nitric acid, and phosphoric acid, and carboxylic acids such as acetic acid, citric acid, gluconic acid, glucoheptonic acid, and lactic acid), basic compounds (e.g., ammonia, alkali metal and alkaline earth metal hydroxides, primary, secondary, or tertiary amines, and primary, secondary, or tertiary alkanolamines), ethyl alcohol, glycerol, glucose, galactose, inositol, mannitol, glactitol, adonitol, arabitol, and amino acids.

3.5 Density Modifiers. The density of the capsule slurry and/or the oil core can be adjusted so that the capsule composition has a substantially uniform distribution of the capsules using known density modifiers or technologies such as those described in Patent Application Publications WO 2000/059616, EP 1502646, and EP 2204155. Suitable density modifiers include hydrophobic materials and materials having a desired molecular weight (e.g., higher than about 12,000), such as silicone oils, petrolatums, vegetable oils, especially sunflower oil and rapeseed oil, and hydrophobic solvents having a desired density (e.g., less than about 1,000 Kg/m³ at 25° C., such as limonene and octane.

3.6 Stabilizers. In some embodiments, a stabilizer (e.g., a colloidal stabilizer) is added to a capsule delivery system to stabilize the emulsion and/or capsule slurry. Examples of colloidal stabilizers are polyvinyl alcohol, cellulose derivatives such hydroxyethyl cellulose, polyethylene oxide, copolymers of polyethylene oxide and polyethylene or polypropylene oxide, or copolymers of acrylamide and acrylic acid. In other embodiments, a stabilizing agent (i.e., a stabilizer) is added to the capsule delivery system to improve the stability of the delivery system for an extended period of storage. When one of these delivery system is added to a consumer product such as a liquid fabric softener/freshener and liquid detergent, this delivery system will also improve the viscosity stability of the consumer product, thus extend the shelf life of the product.

Useful stabilizing agents include multi-functional amines, amino acids/peptides, monofunctional amines, polymers, and a polymeric mixture. These stabilizing agents are in presence in the compositions as free compounds, which are not covalently attached to the capsule walls, being part of the capsule walls, or encapsulated in capsules.

Multi-functional amines are those having at least an amine group (primary, secondary, or tertiary) and one or more other functional groups such as an amine and hydroxyl group. Exemplary multi-functional amines include hexamethylenediamine, hexaethylenediamine, ethylenediamine, 1,3-diaminopropane, 1,4-diamino-butane, diethylenetriamine, pentaethylenehexamine, bis(3-aminopropyl)amine, bis(hexamethylene)triamine, tris(2-aminoethyl)amine, triethylene-tetramine, N,N'-bis(3-aminopropyl)-1,3-propanediamine, tetraethylenepentamine, amino-2-methyl-1-propanol branched polyethylenimine, chitosan, 1,3-diaminoguanidine, 1,1-dimethylbiguanide, and guanidine. Suitable amino acids/peptides include arginine, lysine, histidine, ornithine, nisin, and gelatin. Suitable stabilizing polymers include polyvinylpyrrolidone, polyvinylpyridine-N-oxide, and polyvinyl imidazolinium. These polymers sometimes are used in combination with a second polymer (e.g., a block copolymer) such that the second polymer.

Monofunctional amines have a single amine group.

Examples include $C_1$-$C_{20}$ primary, secondary, or tertiary amines, each of which typically has a molecular weight of 30 to 800 Daltons (e.g., 31 to 500 Daltons and 31 to 300 Daltons). They can be linear, branched, cyclic, acyclic, saturated, unsaturated, aliphatic, and/or aromatic. Nonlimiting examples are methylamine, dimethylamine, trimethylamine, ethylamine, diethylamine, triethylamine, propylamine, isopropylamine, butylamine, dodecylamine, tetradecylamine, aniline, 4-methylaniline, 2-nitroaniline, diphenyl amine, pyrrolidone, piperidine, and morpholine.

The stabilizing agent in the capsule composition can be present in an amount effective to stabilize the composition and/or the final consumer product containing the composition. This amount can be 1 ppm or greater (e.g., 20 ppm or greater, 20 ppm to 20%, 50 ppm to 10%, 50 ppm to 2%, 50 ppm to 1%, 50 to 2000 ppm, and 50 to 1000 ppm). Its concentration in a consumer product can be 20 ppm to 2% (e.g., 50 ppm to 2%, 50 ppm to 1%, 50 to 2000 ppm, and 50 to 1000 ppm).

3.7 Humectants. One or more humectants are optionally included to hold water in the capsule composition for a long period of time. Examples include glycerin, propylene glycol, alkyl phosphate esters, quaternary amines, inorganic salts (e.g., potassium polymetaphosphate, sodium chloride, etc.), polyethylene glycols, and the like.

Further suitable humectants, as well as viscosity control/suspending agents, are disclosed in U.S. Pat. Nos. 4,428, 869, 4,464,271, 4,446,032, and 6,930,078. Details of hydrophobic silicas as a functional delivery vehicle of active materials other than a free flow/anticaking agent are disclosed in U.S. Pat. Nos. 5,500,223 and 6,608,017.

3.8 pH Modifiers. In some embodiments, one or more pH modifiers are included in the capsule composition to adjust the pH value of the capsule slurry and/or the capsule cores. The pH modifiers can also assist in the formation of capsule walls by changing the reaction rate of the crosslinking reactions that form the capsule walls. Exemplary pH modifiers include metal hydroxides (e.g., LiOH, NaOH, KOH, and $Mg(OH)_2$), metal carbonates and bicarbonates ($CSCO_3$, $Li_2CO_3$, $K_2CO_3$, $NaHCO_3$, and CaCO3), metal phosphates/hydrogen phosphates/dihydrogen phosphates, metal sulfates, ammonia, mineral acids (HCl, $H_2S0_4$, $H_3PO_4$, and $HNO_3$), carboxylic acids (e.g., acetic acid, citric acid, lactic acid, benzoic acid, and sulfonic acids), and amino acids.

The level of the adjunct materials can be present at a level of 0.01 to 25% (e.g., from 0.5% to 10%) or greater than 10% (e.g., greater than 30% and greater than 70%).

4. Deposition Aids. A capsule deposition aid from 0.01 to 25%, more preferably from 5 to 20% can be included by weight of the capsule. The capsule deposition aid can be added during the preparation of the capsules or it can be added after the capsules have been made.

These deposition aids are used to aid in deposition of capsules to surfaces such as fabric, hair or skin. These include anionically, cationically, nonionically, or amphoteric water-soluble polymers. Those skilled in the art would appreciate that the charge of these polymers can be adjusted by changing the pH, depending on the product in which this technology is to be used. Any suitable method for coating the deposition aids onto the encapsulated fragrance materials can be used. The nature of suitable polymers for assisted capsule delivery to interfaces depends on the compatibility with the capsule wall chemistry since there has to be some association to the capsule wall. This association can be through physical interactions, such as hydrogen bonding, ionic interactions, hydrophobic interactions, electron transfer interactions or, alternatively, the polymer coating could be chemically (covalently) grafted to the capsule or particle surface. Chemical modification of the capsule or particle surface is another way to optimize anchoring of the polymer coating to capsule or particle surface. Furthermore, the capsule and the polymer need to be compatible with the chemistry (polarity, for instance) of the desired interface. Therefore, depending on which capsule chemistry and interface (e.g., cotton, polyester, hair, skin, wool), the polymer can be selected from one or more polymers with an overall zero (amphoteric: mixture of cationic and anionic functional groups) or net positive charge, based on the following polymer backbones: polysaccharides, polypeptides, polycarbonates, polyesters, polyolefinic (vinyl, acrylic, acrylamide, poly diene), polyester, polyether, polyurethane, polyoxazoline, polyamine, silicone, polyphosphazine, polyaromatic, polyheterocyclic, or polyionene, with molecular weight (MW) ranging from about 1,000 to about 1,000,000,000, preferably from about 5,000 to about 10,000,000. As used herein, molecular weight is provided as weight average molecular weight.

Particular examples of cationic polymers that can be used to coat the polyurea or polyurethane capsule include, e.g., polysaccharides such as guar, alginates, starch, xanthan, chitosan, cellulose, dextrans, arabic gum, carrageenan, and hyaluronates. These polysaccharides can be employed with cationic modification and alkoxy-cationic modifications such as cationic hydroxyethyl or cationic hydroxypropyl.

For example, cationic reagents of choice are 3-chloro-2-hydroxypropyl trimethylammonium chloride or its epoxy version. Another example is graft-copolymers of polyDADMAC on cellulose. Alternatively, polysaccharides can be employed with aldehyde, carboxyl, succinate, acetate, alkyl, amide, sulfonate, ethoxy, propoxy, butoxy, and combinations of these functionalities; or any hydrophobic modification (compared to the polarity of the polysaccharide backbone). The above modifications can be in any ratio and the degree of functionalization can be up to complete substitution of all functionalizable groups, as long as the theoretical net charge of the polymer is zero (mixture of cationic and anionic functional groups) or preferably positive. Furthermore, up to 5 different types of functional groups may be attached to the polysaccharides. Also, polymer graft chains may be differently modified to the backbone. The counterions can be any halide ion or organic counter ion. See U.S. Pat. Nos. 6,297,203 and 6,200,554.

Another source of cationic polymers contain protonatable amine groups so that the overall net charge is zero (amphoteric: mixture of cationic and anionic functional groups) or positive. The pH during use will determine the overall net charge of the polymer. Examples include silk protein, zein, gelatin, keratin, collagen and any polypeptide, such as polylysine.

Further cationic polymers include polyvinyl polymers with up to 5 different types of monomers can be used. The monomers of such polymer have the generic formula:

$$-C(R_2)(R_1)-CR_2R_3-$$

wherein, $R_1$ is H, $C_1$-$C_{25}$ alkane, $C_1$-$C_{25}$ alkene (in which the number of double bonds ranges from 1-5), $C_1$-$C_{25}$ alkoxylated fatty alcohol, or a liquid crystalline moiety that can provide the polymer with thermotropic liquid crystalline properties;

$R^2$ is H or $CH_3$; and $R_3$ is $-Cl$, $-NH_2$ (i.e., polyvinyl amine or its copolymers with N-vinyl formamide.

Such polyvinyl polymers are sold under the name Lupamin 9095 by BASF Corporation. Further suitable cationic polymers containing hydroxylalkylvinylamine units, as disclosed in U.S. Pat. No. 6,057,404.

Another class of materials are polyacrylates with up to 5 different types of monomers. Monomers of polyacrylates have the generic formula:

$$-CH(R_1)-C(R_2)(CO-R_3-R_4)-$$

wherein, $R_1$ is H, $C_1$-$C_{25}$ alkane, $C_1$-$C_{25}$ alkene (in which the number of double bonds ranges from 1-5), $C_1$-$C_{25}$ alkoxylated fatty alcohol, or a liquid crystalline moiety that can provide the polymer with thermotropic liquid crystalline properties;

$R^2$ is H or $CH_3$;

$R^3$ is a $C_1$-$C_{25}$ alkyl alcohol or an alkylene oxide with any number of double bonds, or $R_3$ may be absent such that the C=O bond is (via the C-atom) directly connected to $R_4$; and $R^4$ is $-NH_2$, $-NHR_1$, $-NR_1R_2R_6$ (where $R_6=R^1$, $R_2$, or $-CH_2-COOH$ or its salt), $-NH-C(O)-$, sulfobetaine, betaine, polyethylene oxide, poly(ethyleneoxide/propylene oxide/butylene oxide) grafts with any end group, H, OH, styrene sulfonate, pyridine, quaternized pyridine, alkyl-substituted pyrrolidone or pyridine, pyridine-N-oxide, imidazolinium halide, imidazolium halide, imidazol, piperidine, $-OR_1$, $-OH$, $-COOH$ alkali salt, sulfonate, ethoxy sulphate, pyrrolidone, caprolactam, phenyl-$R_4$ or naphthalene-$R_5$, where $R_4$ and $R_5$ are $R_1$, $R_2$, $R_3$, sulfonic acid or its alkali salt or organic counter ion. Also, glyoxylated cationic polyacrylamides can be used. Typical polymers of choice are those containing the cationic monomer dimethylaminoethyl methacrylate (DMAEMA) or methacrylamidopropyl trimethyl ammonium chloride (MAPTAC) DMAEMA can be found in GAFQUAT® and Gaffix VC-713 polymers from ISP. MAPTAC can be found in BASF's Luviquat PQ11 PN and ISP's GAFQUAT® HS100.

Another group of polymers that can be used are those that contain cationic groups in the main chain or backbone. Included in this group are:

i) polyalkylene imines such as polyethylene imine, commercially available as Lupasol from BASF. Any molecular weight and any degree of crosslinking of this polymer can be used in the present invention;

ii) ionenes as disclosed in U.S. Pat. Nos. 4,395,541 and 4,597,962;

iii) adipic acid/dimethyl amino hydroxypropyl diethylene triamine copolymers, such as CARTARETIN® F-4 and F-23, commercially available from Sandoz;

iv) polymers of the general formula: $-[N(CH_3)_2-(CH_2)_x-\ -NH-(CO)-NH-(CH_2)_y-N(CH_3)_2)-(CH_2)_z-O-(-CH_2)_p]_n-$, with x, y, z, p=1-12, and n according to the molecular weight requirements. Examples are Polyquaternium-2 (MIRAPOL® A-15), Polyquater-nium-17 (MIRAPOL® AD-1), and Polyquaternium-18 (MIRAPOL® AZ-1). Other polymers include cationic polysiloxanes and cationic polysiloxanes with carbon-based grafts with a net theoretical positive charge or equal to zero (mixture of cationic and anionic functional groups). This includes cationic end-group functionalized silicones (i.e., Polyquaternium-80). Silicones with general structure: $-Si(R_1)(R_2)-O-]_x-[Si(R_3)(R_2)-O-]_y-$ where $R_1$ is any alkane from $C_1$-$C_{25}$ or H with number of double bonds from 0-5, aromatic moieties, polysiloxane grafts, or mixtures thereof. $R_1$ can also be a liquid crystalline moiety that can provide the polymer with thermotropic liquid crystalline properties. $R_2$ can be H or $CH_3$; and $R_3$ can be $-R_1-R_4$, where $R_4$ can be $-NH_2$, $-NHR_1$, $-NR_1R_2R_6$ (where $R_6=R_1$, $R_2$, or $-CH_2-COOH$ or its salt), $-NH-C(O)-$, $-COOH$, $-COO-$ alkali salt, any $C_1$-$C_{25}$ alcohol, $-C(O)-NH_2$ (amide), $-C(O)-N(R_2)(R_2')(R_2'')$, sulfobetaine, betaine, polyethylene oxide, poly(ethyleneoxide/propylene oxide/butylene oxide) grafts with any end group, H, $-OH$, styrene sulfonate, pyridine, quaternized pyridine, alkyl-substituted pyrrolidone or pyridine, pyridine-N-oxide, imidazolinium halide, imidazolium halide, imidazol, piperidine, pyrrolidone, caprolactam, sulfonate, ethoxysulphate phenyl-$R_5$ or naphthalene-$R_6$ where $R_5$ and $R_6$ are $R_1$, $R_2$, $R_3$, sulfonic acid or its alkali salt or organic counter ion. $R_3$ can also be $-(CH_2)_x-O-CH_2-CH(OH)-CH_2-N(CH_3)_2-CH_2-COOH$ and its salts. Any mixture of these $R_3$ groups can be selected. X and y can be varied as long as the theoretical net charge of the polymer is zero (amphoteric) or positive. In addition, polysiloxanes containing up to 5 different types of monomeric units may be used. Examples of suitable polysiloxanes are found in U.S. Pat. Nos. 4,395,541, 4,597,962 and 6,200,554. Another group of polymers that can be used to improve capsule/particle deposition are phospholipids that are modified with cationic polysiloxanes. Examples of these polymers are found in U.S. Pat. No. 5,849,313, WO Patent Application 95/18096A1 and European Patent No. 0737183B1.

Furthermore, copolymers of silicones and polysaccharides and proteins can be used (e.g., those commercially available as CRODASONE® brand products).

Another class of polymers includes polyethylene oxide-co-propyleneoxide-co-butylene oxide polymers of any ethylene oxide/propylene oxide/butylene oxide ratio with cationic groups resulting in a net theoretical positive charge or equal to zero (amphoteric). Examples of such polymers are the commercially available TETRONIC® brand polymers.

Suitable polyheterocyclic (the different molecules appearing in the backbone) polymers include the piperazine-alkylene main chain copolymers disclosed by Kashiki & Suzuki (1986) Ind. Eng. Chem. Fundam. 25:120-125.

Cationic PQ polymers shown in Table 1 above can also be used as a deposition aid. Additional suitable PQ polymers are listed in Table 2 below.

TABLE 2

| | Deposition Aids - PQ Polymers | |
|---|---|---|
| PQ | Description | Commercial Products |
| 12 | 2-Propenoic Acid, 2-Methyl-, Decahydro-1,4-Dimethyl-7-(1-Methylethyl)-1-Phenanthrenyl) Methyl Ester, Polymer with 2-(Diethylamino) Ethyl 2-Methyl-2-Propenoate and Ethyl 2-Methyl-2-Propenoate, compd. with Dimethyl Sulfate | |
| 13 | 2-Propenoic Acid, 2-Methyl-, 2-(Diethylamino) Ethyl Ester, Polymer with Ethyl 2-Methyl-2-Propenoate and 9-Octadecenyl 2-Methyl-2-Propenoate, compd. with Dimethyl Sulfate | |
| 22 | Copolymer of Acrylic Acid and Diallyldimethylammonium Chloride | MERQUAT® 280, 281, 280SD, 295 |
| 36 | 2-Propenoic Acid, 2-Methyl-,2-(Dimethylamino) Ethyl Ester, Polymer with Methyl2-Methyl-2-Propenoate, compd. with Dimethyl Sulfate | Plex 4739L (Rohm GmbH) |
| 39 | 2-Propen-1-aminium, N,N-Dimethyl-N-2-Propenyl-, Chloride, Polymer with 2-Propenamide and 2-Propenoic Acid | MERQUAT® 3940, PLUS-3330, PLUS-3331, 3331PR |
| 43 | Polymeric quaternary ammonium salt formed from acrylamide, acrylamidopropyltrimonium chloride, 2-amidopropylacrylamide sulfonate, and DMAPA monomers | GENAMIN® PQ 43 (Clariant Functional Chemicals), Bozequat 4000 (Clariant) |
| 51 | 3,5,8-Triox-4-Phosphaundec-10-en-1-aminium, 4-Hydroxy-N,N,N,10-Tetramethyl-9-Oxo, Inner Salt, 4-Oxide, Polymer with Butyl2-Methyl-2-Propenoate | LIPIDURE® PMB (NOF) |
| 53 | Acrylic Acid/Acrylamide/Methacryl-amidopropyltrimonium Chloride Copolymer | MERQUAT® 2003PR |
| 54 | Aspartic acid, polymer with C6-18 alkylamine, 3-dimethylaminopropylamine and sodium chloroacetate | Quilty-Hy (Mitsui) |
| 58 | 2-Propenoic Acid, Methyl Ester, Polymer with 2,2-Bis [(2-Propenyloxy)Methyl]-1-Butanol and Diethenylbenzene, Reaction Products with N,N-Dimethyl-1,3-Propane-diamine, Chloromethane-Quaternized | Lowenol Conditioner PWW (Lowenstein) - PQ-58 and Wheat Protein |
| 63 | Polymeric quaternary ammonium salt formed by acrylamide, acrylic acid and ethyltrimonium chloride acrylate | Finquat (Innospec), Octacare PQ63 (Innospec Edison, NJ), OF-308 (WSP Chemical & Technology) |
| 65 | 2-Methyl-2-propenoyloxyethyl N,N,N-trimethylammonioethyl phosphate inner salt, polymer with butyl 2-methyl-2-propenoate and sodium 2-methyl-2-propenoate | LIPIDURE®-A (NOF) |
| 66 | 5-Isocyanato-1-(isocyanatomethyl)-1,3,3-trimethylcyclohexane, polymer with di (hydroxypolymethylene) benzenedicarboxylate and ethylbis (2-hydroxyethyl) methylammonium ethyl sulfate | WBR-2925C (Taisei) - PQ-66 and Methyl Pyrrolidone |
| 70 | Polymeric quaternary ammonium salt consisting of an ethoxylated, propoxylated stearyl amine condensed with adipic acid and dilinoleic acid and quaternized with dimethyl sulfate | LUSTREPLEX® (Croda) |
| 76 | | MIRAPOL AT -1 (Rhodia) |
| 86 | Polymeric quaternary ammonium salt of vinylpyrrolidone, 1-methyl-3-vinylimidazoline chloride, vinylimidazole and methacrylic acid | Luvigel Advanced (BASF) |
| 89 | Polymeric quaternary ammonium salt prepared by the reaction oft-butyl acrylate, vinyl pyrolidone, dimethylaminopropyl methacrylamide, methacrylic acid and ethyldimethyl [2-[(2-methyl-loxoallyl) oxy]ammonium ethyl sulfate, neutralized with orthophosphoric acid | (BASF) |
| 94 | Polymeric quaternary ammonium salt consisting of acrylamide, dimethyl diallyl ammonium chloride and methacrylamidopropyltrimonium chloride monomers | (Toho) |
| 95 | Copolymer of Zea Mays (Corn) Starch, Acrylic Acid and acrylamidopropyltrimethylammoniumx chloride monomers | POLYQUART® Ecoclean (Cognis) |
| 98 | | (Cognis GmbH) |

Other suitable deposition aids include those described in US 2013/0330292, US 2013/0337023, US 2014/0017278.

5. Microcapsule Delivery System Formulations. The microcapsule can be formulated into a capsule delivery system (e.g., a microcapsule composition) for use in consumer products.

5.1 Microcapsule Slurry. The capsule delivery system can be a slurry containing in an external hydrophilic solvent (e.g., water and ethanol) the capsule at a level 0.1 to 80% (preferably 1 to 65% and more preferably 5 to 45%) by weight of the capsule delivery system.

In some embodiments, the capsule and its slurry prepared in accordance with the present invention is subsequently purified. Purification can be achieved by washing the capsule slurry with water, e.g., deionized or double deionized water, until a neutral pH is achieved. For the purposes of the present invention, the capsule suspension can be washed using any conventional method including the use of a separatory funnel, filter paper, centrifugation and the like. The capsule suspension can be washed one, two, three, four, five, six, or more times until a neutral pH, e.g., pH 6-8 and 6.5-7.5, is achieved. The pH of the purified capsules can be determined using any conventional method including, but not limited to pH paper, pH indicators, or a pH meter.

A capsule suspension of this invention is "purified" in that it is 80%, 90%, 95%, 97%, 98% or 99% homogeneous to capsules. In accordance with the present invention, purity is achieved by washing the capsules until a neutral pH is achieved, which is indicative of removal of unwanted impurities and/or starting materials, e.g., polyisocyanate, cross-linking agent and the like.

In certain embodiments, the purification of the capsules includes the additional step of adding a salt to the capsule suspension prior to the step of washing the capsule suspension with water. Exemplary salts of use in this step of the invention include, but are not limited to, sodium chloride, potassium chloride or bi-sulphite salts. See US 2014/0017287.

5.2 Spray Drying. The delivery system can also be spray dried to a solid form. In a spray drying process, a spray dry carrier is added to a capsule delivery system to assist the removal of water from the slurry.

According to one embodiment, the spray dry carriers can be selected from the group consisting of carbohydrates such as chemically modified starches and/or hydrolyzed starches, gums such as gum arabic, proteins such as whey protein, cellulose derivatives, clays, synthetic water-soluble polymers and/or copolymers such as polyvinyl pyrrolidone, polyvinyl alcohol. The spray dry carriers may be present in an amount from 1 to 50%, more preferably from 5 to 20%.

Optionally, a free flow agent (anticaking agent) of silicas which may be hydrophobic (i.e. silanol surface treated with halogen silanes, alkoxysilanes, silazanes, siloxanes, etc. such as SIPERNAT® D17, AEROSIL® R972 and R974 (available from Degussa), etc.) and/or hydrophilic such as AEROSIL® 200, SIPERNAT® 22S, SIPERNAT® 50S, (available from Degussa), SYLOID®244 (available from Grace Davison), may be present from about 0.01% to about 10%, more preferable from 0.5% to about 5%.

Humectants and viscosity control/suspending agents can also be added to facilitate spray drying. These agents are disclosed in U.S. Pat. Nos. 4,428,869, 4,464,271, 4,446,032, and 6,930,078. Details of hydrophobic silicas as a functional delivery vehicle of active materials other than a free flow/anticaking agent are disclosed in U.S. Pat. Nos. 5,500,223 and 6,608,017.

The spray drying inlet temperature is in the range of 150 to 240° C., preferably between 17° and 230° C., more preferably between 19° and 220° C.

As described herein, the spray-dried capsule delivery system is well suited for use in a variety of all dry (anhydrous) products: powder laundry detergent, fabric softener dryer sheets, household cleaning dry wipes, powder dish detergent, floor cleaning cloths, or any dry form of personal care products (e.g., shampoo powder, deodorant powder, foot powder, soap powder, baby powder), etc. Because of high fragrance and/or active agent concentration in the spray-dried products of the present invention, characteristics of the aforementioned consumer dry products will not be adversely affected by a small dosage of the spray-dried products.

The capsule delivery system can also be sprayed as a slurry onto a consumer product, e.g., a fabric care product. By way of illustration, a liquid delivery system containing capsules is sprayed onto a detergent powder during blending to make granules. See US 2011/0190191. In order to increase fragrance load, water-absorbing material, such as zeolite, can be added to the delivery system.

Alternatively, granulates in a consumer product are prepared in a mechanical granulator in the presence of a granulation auxiliary such as non-acid water-soluble organic crystalline solids. See WO 2005/097962.

6. Additional Components. The capsule delivery system can also contain one or more other delivery system such as polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof. The capsule delivery system can also contain one or more (e.g., two, three, four, five or six more) different capsules including different capsules of this invention and other capsules such as such as aminoplasts, hydrogel, sol-gel, coacervate capsules, polyurea/polyurethane capsules, and melamine formaldehyde capsules. More exemplary delivery systems that can be incorporated are coacervate capsules, cyclodextrin delivery systems, and pro-perfumes.

6.1 Melt Extruded Flavor/Fragrance. Polymer assisted delivery system include melt extruded flavor/fragrance utilizing high molecular weight carbohydrates, low molecular weight carbohydrates, or polymer.

6.1.1 High molecular weight carbohydrate including starches, modified starches.

6.1.2 Low molecular weight carbohydrates of a low molecular weight carbohydrate or polyol, wherein said low molecular weight carbohydrate or polyol is selected from the group consisting of glucose, sucrose, maltose, lactose, corn syrup solid, erythritol, lactitol, mannitol, sorbitol, maltitol, isomalt, xylitol, trehalose, hydrogenated corn syrup, hydrogenated glucose syrup, hydrogenated maltose syrup, hydrogenated lactose syrup, starch hydrolysate, and a mixture thereof, and wherein said glassy matrix has a glass transition temperature of greater than room temperature.

6.1.3 Polymers (various polymers are useful in the practice of our invention. Specific examples of polymers useful in the practice of our invention are as follows: Dylan low density polyethylene (Atlantic Richfield Company of Los Angeles, CA), DYLITE® of expandable polystyrene compositions (DYLITE® is a trademark of the Atlantic Richfield Company of Los Angeles, CA), Super Dylan high density polyethylene (Atlantic Richfield Company of Los Angeles, CA). Blended polyethylene and carbon black as specifically taught in U.S. Pat. No. 4,369,267. Polystyrene as disclosed in U.S. Pat. No. 4,369,227. Polyene/alpha-olefin copolymers as exemplified and disclosed in U.S. Pat. No. 4,369,291. Poly-alpha-olefins as exemplified in Canadian Letters Pat. Nos. 1,137,069 and 1,137,067. Polymeric compositions as disclosed in Canadian Letters Pat. No. 1,137,068. Polyolefins described in Canadian Letters Pat. Nos. 1,137,066 and 1,139,738. Polyethylene oxides as disclosed in Canadian Letters Pat. No. 1,137,065. Olefin polymers and co-polymers as disclosed in Canadian Letters Pat. No. 1,139,737. Chlorinated PVC as disclosed in Polymer 1982, 23 (7, Suppl.), 1051-6. Polyepsilon caprolactone co-polymers made by means of alcohol initiated polymerization as disclosed in J. Polym. Sci. Polym. Chem. Ed. 1982, 20(2), pages 319-26. Styrene acrylonitrile co-polymers as disclosed in Diss. Abstracts, Int. B, 1982, 42(8), 3346 and abstracted at Chem. Abstracts 96:143750n (1982). Co-polymers of epsilon caprolactone with 1,4-butane diol as disclosed at Kauch. Rezine, 1982, (2), 8-9, abstracted at Chem. Abstracts, volume 96:182506 g (1982). Polyesters as disclosed in U.S. Pat. No. 4,326,010. Chlorinated polyethylene as disclosed by Belorgey, et. al. J. Polym. Sci. Polym. Phys. Ed. 1982, 20(2), 191-203. Plasticized polyepsilon caprolactone co-polymers containing dimethyl phthalate plasticizers as set forth in Japanese Pat. No. J81/147844. Maleic anhydride modified adducts of polyepsilon caprolactone polyols and ethylenically unsaturated monomer as disclosed in U.S. Pat. No. 4,137,279. Polyurethane polymers having lactone backbones as disclosed in U.S. Pat. No. 4,156,067. Polyurethane polyether resins wherein the resin is obtained by reacting a polyfunctional lactone with a long chain polyalkylene diol and a urethane precursor as disclosed in U.S. Pat. No. 4,355,550. Resins having polyurethane backbones as disclosed in U.S. Pat. No. 3,975,350.

6.1.4 Suitable plasticizers include water; glycerol; propylene glycol; aqueous solutions of glycerol, propylene glycol, monosaccharides, and disaccharides; and invert and high fructose corn syrups.

6.1.5 Emulsifier. surface-active agent, i.e., an emulsifier can be added to the dry blend, or preferably added to the liquid flavor mix which is ultimately injected into the metering zone of the extruder. These emulsifiers can be from the class of distilled monoglycerides, mono- and diglyceride blends, propyleneglycol monoglycerides, lecithin, modified lecithins, acetylated monoglycerides, lactylated monoglycerides, lactylated propyleneglycol monoglycerides, sorbitan esters, sorbitan-polyoxyethylene [20] monoglycerides, polyglycerol esters, DATEM's (diacetyltartarate esters of monoglycerides), succinylated esters of monoglycerides and polyoxyethylenepropylene copolymers and mixtures thereof. Most preferred surfactants are the sorbitan-polyoxyethylene [20] monoglycerides, lecithins, and polyglycerol esters.

6.2 Spray Dry Encapsulation.

6.2.1 The matrix is comprised of one or more of the following materials: sugars such as glucose, fructose, lactose, galactose, ribose, xylose, sucrose, maltose; polyols such as glycerin and propylene glycol; corn syrups, maltodextrin, fats, silicone dioxide, polyhydric alcohols, corn syrup solids, starches, modified starches, emulsifiers and food acids. The level of maltodextrin used in the matrix, comprises from about 25 to about 98 weight percent, preferably form about 35 to about 75 weight percent, the maltodextrin.

6.2.2 Core modifiers: flavors and fragrance may also be combined with a variety of solvents which serve to increase the compatibility of the various materials, increase the overall hydrophobicity of the blend, influence the vapor pressure of the materials, or serve to structure the blend. Solvents performing these functions are well known in the art and include mineral oils, triglyceride oils, silicone oils, fats, waxes, fatty alcohols, diisodecyl adipate, and diethyl phthalate among others.

6.2.3 emulsifiers including monoglycerides of fatty acids, distilled succinylated monoglycerides of fatty acids, sorbitan fatty acid esters; distilled acetylated monoglycerides of fatty acids, monoglycerides of fatty acids.

6.3 Coascervate Capsules.

6.3.1 Proteins useful in coacervation processes include albumins, vegetable globulins and gelatines. The gelatine may be fish, pork, beef, and/or poultry gelatine, for example. According to a preferred embodiment, the protein is fish, beef or poultry gelatine. According to a more preferred embodiment, the protein is warm water fish gelatine.

6.3.2 Typical non-protein polymers useful in complex coacervation methods include, in particular, negatively charged polymers. For example, they may be selected from gum arabic, xanthan, agar, alginate salts, cellulose derivatives, for example carboxymethyl cellulose, pectinate salts, carrageenan, polyacrylic and methacrylic acid, and/or mixtures thereof. Further suitable non-proteins can be derived from the literature, for example from to WO 2004/022221, page 4, lines 27-29.

6.3.3 A cross-linking agent is typically used to harden the coating layer. Suitable cross-linking agents include formaldehyde, acetaldehyde, glutaraldehyde, glyoxal, chrome alum, or transglutaminase. Preferably, transglutaminase is used at 10-100, preferably 30-60 activity units per gram of gelatine. This enzyme is well described and commercially obtainable.

6.4 Cyclodextrin Delivery System This technology approach uses a cyclic oligosaccharide or cyclodextrin to improve the delivery of perfume. Typically, a perfume and cyclodextrin (CD) complex is formed. Such complexes may be preformed, formed in-situ, or formed on or in the situs. See, e.g., WO 2013/109798 A2 and US 2011/0308556 A1.

6.5 Pro-Perfume 6.5.1 Michael Addition reaction products of a primary/secondary amine with an unsaturated ester, acid or nitrile perfume compound such those described in U.S. Pat. No. 6,858,575.

6.5.2 Reaction product between a primary/secondary amine compound/polymer and a ketone or aldehyde perfume compound such as those described in WO 2001/051599 A1 and WO 2002/092746 A1.

6.5.3 other nonlimiting examples include aromatic or non-aromatic imines (Schiff bases), oxazolidines, beta-keto esters, orthoesters, compounds comprising one or more beta-oxy or beta-thio carbonyl moieties capable of releasing a perfume (e.g., an alpha, beta-unsaturated ketone, aldehyde or carboxylic ester). The typical trigger for perfume release is exposure to water; although other triggers may include enzymes, heat, light, pH change, autoxidation, a shift of equilibrium, change in concentration or ionic strength and others. Suitable pro-perfumes and methods of making same can be found in U.S. Pat. Nos. 8,912,350 B2, 7,018,978 B2; 6,987,084 B2; 6,956,013 B2; 6,861,402 B1; 6,544,945 B1; U.S. Pat. Nos. 6,093,691; 6,277,796 B1; U.S. Pat. Nos. 6,165,953; 6,316,397 B1; 6,437,150 B1; 6,479,682 B1; U.S. Pat. Nos. 6,096,918; 6,218,355 B1; U.S. Pat. Nos. 6,133, 228; 6,147,037; 7,109,153 B2; 7,071,151 B2; 6,987,084 B2; 6,916,769 B2; 6,610,646 B2 and 5,958,870, as well as can be found in US 2005/0003980 A1 and US 2006/0223726 A1.

Any compound, polymer, or agent discussed above can be the compound, polymer, or agent itself as shown above, or its salt, precursor, hydrate, or solvate. A salt can be formed between an anion and a positively charged group on the compound, polymer, or agent. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group on the compound, polymer, or agent. Suitable cations include sodium ion, potassium ion, magnesium ion, calcium ion, and an ammonium cation (e.g., tetramethylammonium ion). A precursor can be ester and another suitable derivative, which, during the process of preparing a polyurea or polyurethane capsule composition of this invention, is capable of converting to the compound, polymer, or agent and being used in preparing the polyurea or polyurethane capsule composition. A hydrate refers to the compound, polymer, or agent that contains water. A solvate refers to a complex formed between the compound, polymer, or agent and a suitable solvent. A suitable solvent can be water, ethanol, isopropanol, ethyl acetate, acetic acid, and ethanolamine.

Certain compounds, polymers, and agents have one or more stereocenters, each of which can be in the R configuration, the S configuration, or a mixture. Further, some compounds, polymers, and agents possess one or more double bonds wherein each double bond exists in the E (trans) or Z (cis) configuration, or combinations thereof. The compounds, polymers, and agents include all possible configurational stereoisomeric, regioisomeric, diastereomeric, enantiomeric, and epimeric forms as well as any mixtures thereof. As such, lysine used herein includes L-lysine, D-lysine, L-lysine monohydrochloride, D-lysine monohydrochloride, lysine carbonate, and so on. Similarly, arginine includes L-arginine, D-arginine, L-arginine monohydrochloride, D-arginine monohydrochloride, arginine carbonate, arginine monohydrate, etc. Guanidine includes guanidine hydrochloride, guanidine carbonate, guanidine thiocyanate, and other guanidine salts including their hydrates. Ornithine include L-ornithine and its salts/hydrates (e.g., monohydrochloride) and D-ornithine and its salts/hydrates (e.g., monohydrochloride).

7. Applications. The delivery systems of the present invention are well-suited for use, without limitation, in the following products:

a) Household Products
  i. Liquid or Powder Laundry Detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. To prepare a powder laundry detergent, a microcapsule composition of this invention as a slurry can be sprayed to an unfragranced powder product. Alternatively, the microcapsule composition can be mixed with the unfragranced powder product and then dried to provide a final powder laundry detergent. See EP 1694810 A1.
  ii. Unit Dose Pouches, Tablets and Capsules such as those described in EP 1 431 382 A1, US 2013/0219996 A1, US 2013/0284637 A1, and U.S. Pat. No. 6,492,315. These unit dose formulations can contain high concentrations of a functional material (e.g., 5-100% fabric softening agent or detergent active), fragrance (e.g., 0.5-100%, 0.5-40%, and 0.5-15%), and flavor (e.g., 0.1-100%, 0.1-40%, and 1-20%). They can contain no water to limit the water content as low as less than 30% (e.g., less than 20%, less than 10%, and less than 5%).
  iii. Scent Boosters such as those described in U.S. Pat. Nos. 7,867,968, 7,871,976, 8,333,289, US 2007/0269651 A1, and US2014/0107010 A1.
  iv. Fabric Care Products such as Rinse Conditioners (containing 1 to 30 weight % of a fabric conditioning active), Fabric Liquid Conditioners (containing 1 to 30 weight % of a fabric conditioning active), Tumble Drier Sheets, Fabric Refreshers, Fabric Refresher Sprays, Ironing Liquids, and Fabric Softener Systems such as those described in U.S. Pat. Nos. 6,335,315, 5,674,832, 5,759,990, 5,877,145, 5,574,179, 5,562,849, 5,545,350, 5,545,340, 5,411,671, 5,403,499, 5,288,417, 4,767,547 and 4,424,134 Liquid fabric softeners/fresheners contain at least one fabric softening agent present, preferably at a concentration of 1 to 30% (e.g., 4 to 20%, 4 to 10%, and 8 to 15%). The ratio between the active material and the fabric softening agent can be 1:500 to 1:2 (e.g., 1:250 to 1:4 and 1:100 to 1:8). As an illustration, when the fabric softening agent is 5% by weight of the fabric softener, the active material is 0.01 to 2.5%, preferably 0.02 to 1.25% and more preferably 0.1 to 0.63%. As another example, when the fabric softening agent is 20% by weight of the fabric softener, the active material is 0.04 to 10%, preferably 0.08 to 5% and more preferably 0.4 to 2.5%. The active material is a fragrance, malodor counteractant or mixture thereof. The liquid fabric softener can have 0.15 to 15% of capsules (e.g., 0.5 to 10%, 0.7 to 5%, and 1 to 3%). When including capsules at these levels, the neat oil equivalent (NOE) in the softener is 0.05 to 5% (e.g., 0.15 to 3.2%, 0.25 to 2%, and 0.3 to 1%).
  Suitable fabric softening agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390. Suitable softening agents include esterquats such as REWOQUAT® WE 18 commercially available from Evonik Industries and STEPANTEX® SP-90 commercially available from Stepan Company.
  v. Liquid dish detergents such as those described in U.S. Pat. Nos. 6,069,122 and 5,990,065.
  vi. Automatic Dish Detergents such as those described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562.
  vii. All-purpose Cleaners including bucket dilutable cleaners and toilet cleaners.
  viii. Bathroom Cleaners.
  ix. Bath Tissue.
  x. Rug Deodorizers.
  xi. Candles.
  xii. Room Deodorizers.
  xiii. Floor Cleaners.
  xiv. Disinfectants.
  xv. Window Cleaners.
  xvi. Garbage bags/trash can liners.
  xvii. Air Fresheners including room deodorizer and car deodorizer, scented candles, sprays, scented oil air freshener, Automatic spray air freshener, and neutralizing gel beads.
  xviii. Moisture absorber.
  xix. Household Devices such as paper towels and disposable Wipes.
  xx. Moth balls/traps/cakes.
b) Baby Care Products.
  i. Diaper Rash Cream/Balm.
  ii. Baby Powder.

c) Baby Care Devices.
   i. Diapers.
   ii. Bibs.
   iii. Wipes.
d) Oral Care Products. Tooth care products (as an example of preparations according to the invention used for oral care) generally include an abrasive system (abrasive or polishing agent), for example silicic acids, calcium carbonates, calcium phosphates, aluminum oxides and/or hydroxylapatites, surface-active substances, for example sodium lauryl sulfate, sodium lauryl sarcosinate and/or cocamidopropylbetaine, humectants, for example glycerol and/or sorbitol, thickening agents, for example carboxymethyl cellulose, polyethylene glycols, carrageenan and/or LAPONITE®, sweeteners, for example saccharin, taste correctors for unpleasant taste sensations, taste correctors for further, normally not unpleasant taste sensations, taste-modulating substances (for example inositol phosphate, nucleotides such as guanosine monophosphate, adenosine monophosphate or other substances such as sodium glutamate or 2-phenoxypropionic acid), cooling active ingredients, for example menthol derivatives, (for example L-menthyllactate, L-menthylalkylcarbonates, menthone ketals, menthane carboxylic acid amides), 2,2,2-trialkylacetic acid amides (for example 2,2-diisopropylpropionic acid methyl amide), icilin and icilin derivatives, stabilizers and active ingredients, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings and/or sodium bicarbonate or taste correctors.
   i. Toothpaste. An exemplary formulation as follows:
      1. calcium phosphate 40-55%
      2. carboxymethyl cellulose 0.8-1.2%
      3. sodium lauryl sulfate 1.5-2.5%
      4. glycerol 20-30%
      5. saccharin 0.1-0.3%
      6. flavor oil 1-2.5%
      7. water q.s. to 100%
   A typical procedure for preparing the formulation includes the steps of (i) mixing by a blender according to the foregoing formulation to provide a toothpaste, and (ii) adding a composition of this invention and blending the resultant mixture till homogeneous.
   ii. Tooth Powder.
   iii. Oral Rinse.
   iv. Tooth Whiteners.
   v. Denture Adhesive.
e) Health Care Devices.
   i. Dental Floss.
   ii. Toothbrushes.
   iii. Respirators.
   iv. Scented/flavored condoms.
f) Feminine Hygiene Products such as Tampons, Feminine Napkins and Wipes, and Pantiliners.
g) Personal Care Products: Cosmetic or pharmaceutical preparations, e.g., a "water-in-oil" (W/O) type emulsion, an "oil-in-water" (O/W) type emulsion or as multiple emulsions, for example the water-in-oil-in-water (W/O/W) type, as a PIT emulsion, a Pickering emulsion, a micro-emulsion or nano-emulsion; and emulsions which are particularly preferred are of the "oil-in-water" (O/W) type or water-in-oil-in-water (W/O/W) type. More specifically,
   i. Personal Cleansers (bar soaps, body washes, and shower gels).
   ii. In-shower conditioner.
   iii. Sunscreen ant tattoo color protection (sprays, lotions, and sticks).
   iv. Insect repellants.
   v. Hand Sanitizer.
   vi. Antiinflammatory balms, ointments, and sprays.
   vii. Antibacterial ointments and creams.
   viii. Sensates.
   ix. Deodorants and Antiperspirants including aerosol and pump spray antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant, gel deodorant, spray deodorant, roll-on, and cream deodorant.
   x. Wax-based Deodorant. An exemplary formulation as follows:
      1. Paraffin Wax 10-20%
      2. Hydrocarbon Wax 5-10%
      3. White Petrolatum 10-15%
      4. Acetylated Lanolin Alcohol 2-4%
      5. Diisopropyl Adipate 4-8%
      6. Mineral Oil 40-60%
      7. Preservative (as needed)
   The formulation is prepared by (i) mixing the above ingredients, (ii) heating the resultant composition to 75° C. until melted, (iii) with stirring, adding 4% cryogenically ground polymer containing a fragrance while maintaining the temperature 75° C., and (iv) stirring the resulting mixture in order to ensure a uniform suspension while a composition of this invention is added to the formulation.
   xi. Glycol/Soap Type Deodorant. An exemplary formulation as follows:
      1. Propylene Glycol 60-70%
      2. Sodium Stearate 5-10%
      3. Distilled Water 20-30%
      4. 2,4,4-Trichloro-2'-Hydroxy Diphenyl Ether, manufactured by the Ciba-Geigy Chemical Company) 0.01-0.5%
   The ingredients are combined and heated to 75° C. with stirring until the sodium stearate has dissolved. The resulting mixture is cooled to 40° C. followed by addition of a composition of this invention.
   xii. Lotion including body lotion, facial lotion, and hand lotion.
   xiii. Body powder and foot powder.
   xiv. Toiletries.
   xv. Body Spray.
   xvi. Shave cream and male grooming products.
   xvii. Bath Soak.
   xviii. Exfoliating Scrub.
h) Personal Care Devices.
   i. Facial Tissues.
   ii. Cleansing wipes.
i) Hair Care Products.
   i. Shampoos (liquid and dry powder).
   ii. Hair Conditioners (Rinse-out conditioners, leave-in conditioners, and cleansing conditioners).
   iii. Hair Rinses.
   iv. Hair Refreshers.

v. Hair perfumes.
vi. Hair straightening products.
vii. Hair styling products, Hair Fixative and styling aids.
viii. Hair combing creams.
ix. Hair wax.
x. Hair foam, hair gel, nonaerosol pump spray.
xi. Hair Bleaches, Dyes and Colorants.
xii. Perming agents.
xiii. Hair wipes.

j) Beauty Care.
  i. Fine Fragrance-Alcoholic. Compositions and methods for incorporating fragrance capsules into alcoholic fine fragrances are described in U.S. Pat. No. 4,428,869. Alcoholic fine fragrances may contain the following:
    1. Ethanol (1-99%)
    2. Water (0-99%)
    3. A suspending aide including but not limited to: hydroxypropyl cellulose, ethyl cellulose, silica, microcrystalline cellulose, carrageenan, propylene glycol alginate, methyl cellulose, sodium carboxymethyl cellulose or xanthan gum (0-1%)
    4. Optionally an emulsifier or an emollient may be included including but not limited to those listed above.
  ii. Solid Perfume.
  iii. Lipstick/lip balm.
  iv. Make-up cleanser.
  v. Skin care cosmetic such as foundation, pack, sunscreen, skin lotion, milky lotion, skin cream, emollients, skin whitening.
  vi. Make-up cosmetic including manicure, mascara, eyeliner, eye shadow, liquid foundation, powder foundation, lipstick and cheek rouge.

k) Consumer goods packaging such as fragranced cartons, fragranced plastic bottles/boxes.

l) Pet care products.
  i. Cat litter.
  ii. Flea and tick treatment products.
  iii. Pet grooming products.
  iv. Pet shampoos.
  v. Pet toys, treats, and chewables.
  vi. Pet training pads.
  vii. Pet carriers and crates.

m) Confectionaries confectionery, preferably selected from the group consisting of chocolate, chocolate bar products, other products in bar form, fruit gums, hard and soft caramels and chewing gum.
  i. Gum.
    1. Gum base (natural latex chicle gum, most current chewing gum bases also presently include elastomers, such as polyvinylacetate (PVA), polyethylene, (low or medium molecular weight) polyisobutene (PIB), polybutadiene, isobutene-isoprene copolymers (butyl rubber), polyvinylethylether (PVE), polyvinylbutyether, copolymers of vinyl esters and vinyl ethers, styrene-butadiene copolymers (styrene-butadiene rubber, SBR), or vinyl elastomers, for example based on vinylacetate/vinyllaurate, vinylacetate/vinylstearate or ethylene/vinylacetate, as well as mixtures of the mentioned elastomers, as described for example in EP 0 242 325, U.S. Pat. Nos. 4,518,615, 5,093,136, 5,266,336, 5,601,858 or U.S. Pat. No. 6,986,709.) 20-25%
    2. Powdered sugar 45-50%
    3. glucose 15-17%
    4. starch syrup 10-13%
    5. plasticizer 0.1%
    6. flavor 0.8-1.2% The components described above were kneaded by a kneader according to the foregoing formulation to provide a chewing gum. Encapsulated Flavor or sensate is then added and blended till homogeneous.
  ii. Breath Fresheners.
  iii. Orally Dissolvable Strips.
  iv. Chewable Candy.
  v. Hard Candy.

n) Baked products, preferably selected from the group consisting of bread, dry biscuits, cakes and other cookies.

o) snack foods, preferably selected from the group consisting of baked or fried potato chips or potato dough products, bread dough products and corn or peanut-based extrudates.
  i. Potato, tortilla, vegetable or multigrain chips.
  ii. Popcorn.
  iii. Pretzels.
  iv. Extruded stacks.

p) Cereal Products preferably selected from the group consisting of breakfast cereals, muesli bars and precooked finished rice products.

q) Alcoholic and non-alcoholic beverages, preferably selected from the group consisting of coffee, tea, wine, beverages containing wine, beer, beverages containing beer, liqueurs, schnapps, brandies, sodas containing fruit, isotonic beverages, soft drinks, nectars, fruit and vegetable juices and fruit or vegetable preparations; instant beverages, preferably selected from the group consisting of instant cocoa beverages, instant tea beverages and instant coffee beverages.
  i. Ready to drink liquid drinks.
  ii. Liquid Drink Concentrates.
  iii. Powder Drinks.
  iv. Coffee: Instant Cappuccino.
    1. Sugar 30-40%
    2. Milk Powder 24-35%
    3. Soluble Coffee 20-25%
    4. Lactose 1-15%
    5. Food Grade Emulsifier 1-3%
    6. Encapsulated Volatile Flavor 0.01-0.5%
  v. Tea.
  vi. Alcoholic.

r) Spice blends and consumer prepared foods.
  i. Powder gravy, sauce mixes.
  ii. Condiments.
  iii. Fermented Products.

s) Ready to heat foods: ready meals and soups, preferably selected from the group consisting of powdered soups, instant soups, precooked soups.
  i. Soups.
  ii. Sauces.
  iii. Stews.
  iv. Frozen entrees.

t) Dairy Products milk products, preferably selected from the group consisting of milk beverages, ice milk, yogurt, kefir, cream cheese, soft cheese, hard cheese, powdered milk, whey, butter, buttermilk and partially or fully hydrolyzed milk protein-containing products Flavored milk beverages.
  i. Yoghurt.
  ii. Ice cream.

iii. Bean Curd.
iv. Cheese.
u) Soya protein or other soybean fractions, preferably selected from the group consisting of soya milk and products produced therefrom, soya lecithin-containing preparations, fermented products such as tofu or tempeh or products produced therefrom and soy sauces.
v) Meat products, preferably selected from the group consisting of ham, fresh or raw sausage preparations, and seasoned or marinated fresh or salt meat products.
w) Eggs or egg products, preferably selected from the group consisting of dried egg, egg white and egg yolk.
x) Oil-based products or emulsions thereof, preferably selected from the group consisting of mayonnaise, remoulade, dressings and seasoning preparations.
y) fruit preparations, preferably selected from the group consisting of jams, sorbets, fruit sauces and fruit fillings; vegetable preparations, preferably selected from the group consisting of ketchup, sauces, dried vegetables, deep-frozen vegetables, precooked vegetables, vegetables in vinegar and preserved vegetables.
z) Flavored pet foods.

The above-listed applications are all well known in the art. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, and 4,767,547, 4,424,134. Liquid laundry detergents include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Liquid dish detergents are described in U.S. Pat. Nos. 6,069,122 and 5,990,065. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. Automatic Dish Detergents are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562.

The terms "polyfunctional isocyanate," "multifunctional isocyanate," and "polyisocyanate" are used interchangeably and refer to a compound having two or more isocyanate (—NCO) groups.

The terms "polyfunctional amine," "multifunctional amine," and "polyamine" are used interchangeably and refer to a compound containing two or more primary or secondary amine groups. These terms also refer to a compound containing one or more primary/secondary amine groups and one or more hydroxyl groups.

The terms "polyfunctional alcohol," "multifunctional alcohol," "poly alcohol," and "polyol" are used interchangeably and refer to a compound having two or more hydroxyl groups.

The invention is described in greater detail by the following non-limiting examples. Without further elaboration, it is believed that one skilled in the art can, based on the description herein, utilize the invention to its fullest extent. All publications cited herein are incorporated by reference in their entirety.

EXAMPLE 1

A microcapsule composition of this invention, i.e., Composition 1, was prepared following the procedure described below.

A polyurea microcapsule, i.e., Microcapsule 1, was first prepared. One hundred and sixty-eight grams of a research fragrance accord (International Flavors and Fragrance, Union Beach, NJ) was weighed out and combined with 42 g of NEOBEE® oil (caprylic/capric triglyceride; Commercially available from Stepan, Chicago, IL, USA) and 16.8 g of isocyanate monomer, LUPRANATE® M20 (BASF corporation, Wyandotte, MI, USA) to form an oil phase. In a separate beaker, an aqueous solution (267.13 g) containing 0.98% MORWET® D-425 (sodium salt of naphthalene sulfonate condensate; Akzo Nobel, Fort Worth, TX, USA) and 0.98% polyvinylpyrrolidone (LUVISKOL® K90, BASF, Ludwigshafen, Germany) was used as an aqueous phase. The oil phase was then emulsified into the aqueous phase to form a fragrance emulsion under shearing (ULTRA TURRAX®, T25 Basic, IKA® WERKE) at 6500 rpm for three minutes.

The fragrance emulsion was heated to 35° C. Hexamethylene diamine ("HMDA", 18.9 g, 40% aqueous solution, INVISTA, Wichita, KS, USA) was added under constant mixing with an overhead mixer. The mixer speed was maintained the same throughout the process. The capsule slurry was cured at 55° C. for two hours. Cooling the slurry to room temperature yielded Microcapsule 1 as a slurry.

Microcapsule 1 thus prepared 525 g was mixed with 12 g of ACULYN® 33 (containing about 28 wt % of a copolymer of acrylic acid and acrylate, commercially available from Dow Chemical, the Netherlands) for 30 minutes. After the pH was adjusted to 8 using 50% citric acid (approximately 6 g used), 36 g of Polyquaternium-6 (PQ-6, MERQUAT® 100 42 wt % aqueous solution, commercially available from Lubrizol, USA) and 21 g of water were added under constant mixing to give Composition 1, which contained 2 wt % ACULYN®33 (i.e., 0.56 wt % of the copolymer of acrylic acid and acrylate) as a viscosity control agent and 2.5 wt % polyquaternium-6 as a deposition aid agent.

EXAMPLES 2-8

Seven additional microcapsule compositions of this invention were prepared as described above.

Composition 2 was prepared following the same procedure as Composition 1 except that 18 g of ACULYN®33 was added to 525 g of Microcapsule 1. Composition 2 thus prepared contained 3 wt % ACULYN®33 (i.e., 0.84 wt % of the copolymer) and 2.5 wt % PQ-6.

Composition 3 was prepared following the same procedure as Composition 1 except that 24 g of ACULYN®33 was added to 525 g of Microcapsule 1. Composition 3 contained 4 wt % ACULYN® 33 (i.e., 1.12 wt % of the copolymer) and 2.5 wt % PQ-6.

Composition 4 was prepared following the same procedure as Composition 1 using, instead of ACULYN®33, 4.2 g of 3% KELTROL® T Plus aqueous solution (xanthan gum, a high molecular weight polysaccharide, commercially available from CP Kelco, Belgium) in 525 g of Microcapsule 1. Composition 4 contained 0.021% KELTROL® T Plus as the viscosity control agent and 2.5 wt % PQ-6.

Composition 5 was prepared following the same procedure as Composition 1 except that 6 g of 3% KELTROL® T Plus solution, instead of ACULYN®33, was added to 525 g of Microcapsule 1. Composition 5 contained 0.03% KELTROL® T Plus and 2.5 wt % PQ-6.

Composition 6 was prepared following the same procedure as Composition 1 except that 9 g of 3% KELTROL® T Plus solution, instead of ACULYN®33, was added to 525 g of Microcapsule 1. Composition 5 contained 0.045% KELTROL® T Plus and 2.5 wt % PQ-6.

Composition 7 was prepared by mixing 525 g of Microcapsule 1 with 18 g of ACULYN®33. Note that no PQ-6 was added. Composition 7 contained 3% ACULYN®33 (i.e., 0.84 wt % of the copolymer).

Composition 8 was prepared by mixing 24 g of ACULYN®33 with 525 g of Microcapsule 1. Composition 8 contained 4% ACULYN®33 (i.e., 1.12 wt % of the copolymer).

Comparative Composition Containing PQ-6. A comparative composition, i.e., Comparative Composition 1', was prepared by mixing 525 g of Microcapsule 1, 36 g of PQ-6 and 39 g of water. Comparative Composition 1' did not contain any viscosity control agent.

Viscosity Measurement. The viscosity of Compositions 7-10 and Microcapsule 1 were measured using a viscometer Anton Paar MCR 302 Rheometer. Before measurement, each sample was stirred with a spatula to ensure homogeneity. After the viscometer performed a pre-shearing for 5 minutes, the viscosity was analyzed at a shear rate of 21 $S^{-1}$. For each sample, 15 viscosity readings were obtained. The average viscosity readings were reported in Tables 5 and 6 below.

Compositions 1-10, Microcapsule 1, and Comparative Composition 1' were evaluated for water separation as an indication of storage stability. After being stored in predetermined conditions, in some samples, water was separated as a layer, which was measured using a graduated cylinder. The water separation was calculated as volume percent (v %) of the water layer as compared to the total volume of the composition including the water layer. The water separation v % results were summarized in Tables 3-7 below.

Microcapsule 1, Comparative Composition 1', and Compositions 1-3 were stored at 4° C. for 4 weeks to evaluate their water separation. The results were summarized in Table 3 below.

TABLE 3

Viscosity and water separation after 4 weeks

| Sample | Viscosity Control Agent, % | v % of Water Separation |
|---|---|---|
| Microcapsule 1 | (None) | 2.8 |
| Comparative 1' | (None) | 1.4 |
| Composition 1 | ACULYN ® 33, 2% | 0 |
| Composition 2 | ACULYN ® 33, 3% | 0 |
| Composition 3 | ACULYN ® 33, 4% | 0 |

In another storage stability evaluation, Microcapsule 1, Comparative Composition 1', and Compositions 5 and 6 were stored at 4° C. for 4 weeks for water separation. The results were summarized in Table 4 below.

In a third storage stability evaluation, Microcapsule 1, and Compositions 7 and 8 were stored at 37° C. for 8 weeks. At the end of the storage, the samples were evaluated for their viscosity and water separation. The results were summarized in Table 5 below.

TABLE 4

Viscosity and water separation after 4 weeks

| Sample | Viscosity Control Agent, % | v % of Water Separation |
|---|---|---|
| Microcapsule 1 | (None) | 4.2 |
| Comparative 1' | (None) | 1.4 |

TABLE 4-continued

Viscosity and water separation after 4 weeks

| Sample | Viscosity Control Agent, % | v % of Water Separation |
|---|---|---|
| Composition 5 | KELTROL ® T Plus, 1% | 0 |
| Composition 6 | KELTROL ® T Plus, 1.5% | 0 |

TABLE 5

Viscosity and water separation at 37° C. after 8 weeks

| Sample | Viscosity Control Agent (%) | Viscosity (cP, at 21 Hz) | Water Separation, % |
|---|---|---|---|
| Microcapsule 1 | (None) | 263 | 8 |
| Composition 7 | ACULYN ® 33, 3% | 557 | 2 |
| Composition 8 | ACULYN ® 33, 4% | 983 | 2 |

EXAMPLES 9 AND 10

ACULYN® 33 can also stabilize microcapsule compositions containing two or more different capsules. Two compositions, i.e., Compositions 9 and 10, were prepared by mixing a melamine-formaldehyde microcapsule, a polyurea microcapsule, and ACULYN® 33 at the level showing in Table 6 below.

The polyurea microcapsule, i.e., Microcapsule 1, was prepared according to the procedure described in Example 1.

A melamine-formaldehyde microcapsule, i.e., Microcapsule 2, was prepared following the procedure described in US20070138673.

More specifically, 80 parts by weight of a research fragrance oil was admixed with 20 parts by weight of NEOBEE® M5 solvent thereby forming a microcapsule core oil. The uncoated capsules were prepared by creating a polymeric wall to encapsulate microcapsule core oil droplets. To make the capsule slurry, a copolymer of acrylamide and acrylic acid was first dispersed in water together with a methylated melamine-formaldehyde resin. These two components were allowed to react under acidic conditions. The microcapsule core oil was then added into the solution and droplets of the desired size were achieved by high shear homogenization. The resultant microcapsule slurry was cured at 80° C. for 1 hour. The resulting microcapsule slurry contained about 55% water and about 45% filled microcapsules (10% microcapsule wall together with 35% the microcapsule core consisting of 80% fragrance oil and 20% NEOBEE® M-5). The thus prepared Microcapsule 3 had a pH of about 5.

Compositions 9 and 10 were evaluated for the viscosity and water separation after stored at 37° C. for 8 weeks. The results were shown in Table 6 below.

EXAMPLES 11-14

In Examples 11-14 below, ACULYN®33 was used to stabilize microcapsule compositions containing melamine-formaldehyde microcapsules.

TABLE 6

Viscosity and water separation at 37° C. after 8 weeks

| Sample | Components, % | Viscosity (cP, at 21 Hz) | Water Separation, % |
|---|---|---|---|
| Composition 9 | Microcapsule 1, 50% Microcapsule 2, 50% ACULYN ® 33, 3% | 860 | 0 |
| Composition 10 | Microcapsule 1, 25% Microcapsule 2, 75% ACULYN ® 33, 3% | 930 | 0 |

Four microcapsule compositions of this invention, i.e., Compositions 11-14, were prepared using Microcapsule 2 and ACULYN®33.

Composition 11 contained 1% ACULYN®33 (i.e., 0.28 wt % of the copolymer of acylic acid and acrylate) by weight of the composition.

Composition 12 contained 2% ACULYN®33 (i.e., 0.56 wt % of the copolymer).

Composition 13 contained 3% ACULYN®33 (i.e., 0.84 wt % of the copolymer).

Composition 14 contained 4% ACULYN® 33 (i.e., 1.12 wt % of the copolymer).

Microcapsule 3 and Compositions 11-14 were stored at 20 or 45° C. for 4 weeks. Their water separation % was measured. The results are shown in Table 7 below.

TABLE 7

Water separation after 4 weeks

| Sample | Viscosity Control agent (%) | Water separation at 20° C., % | Water separation at 45° C., % |
|---|---|---|---|
| Microcapsule 2 | (none) | 5 | 10 |
| Composition 11 | ACULYN ® 33, 1% | 2 | 4 |
| Composition 12 | ACULYN ® 33, 2% | 0 | 1 |
| Composition 13 | ACULYN ® 33, 3% | 0 | 0 |
| Composition 14 | ACULYN ® 33, 4% | 0 | 0 |

Microcapsule 2 and Composition 12 were also stored at 20 or 45° C. for a prolonged time. After 24 weeks at 20° C., Microcapsule 2 had a water separation of 15% by volume of the composition. By contrast, Composition 12 showed only 6% water separation. After 24 weeks at 45° C., Microcapsule 2 had a water separation of 28% and Composition 12 had a water separation of only 8%.

The results above showed that ACULYN® 33 unexpectedly stabilized microcapsules at an elevated temperature (e.g., 45° C.) for a prolonged period of storage.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to achieve the purpose of stabilizing microcapsule composition, one skilled in the art can choose any viscosity control agent described herein and determine its content without undue experimentation.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A core-shell microcapsule composition comprising:
   (a) microcapsules, the core of the microcapsules comprises an active material and the shell of the microcapsules comprises polyurea;
   (b) a dispersant comprising whey protein or pea protein;
   (c) a hydrocolloid comprising gum Arabic or modified starch; and
   (d) a viscosity control agent comprising xanthan gum.

2. The core-shell microcapsule composition of claim 1, wherein the polyurea is present at 0.1 to 5% by weight of the core-shell microcapsule composition.

3. The core-shell microcapsule composition of claim 1, wherein the active material comprises at least one of a fragrance, pro-fragrance, or malodor counteractive agent.

4. A consumer product comprising the core-shell microcapsule composition of claim 1.

5. The consumer product of claim 4, wherein the consumer product is a fabric care product, a fabric softener, a fabric refresher, a liquid laundry detergent, a personal wash, a hair conditioner or a shampoo.

* * * * *